(12) United States Patent
Gao et al.

(10) Patent No.: US 9,119,874 B2
(45) Date of Patent: Sep. 1, 2015

(54) CELL-PENETRATING MARKERS OF APOPTOSIS

(71) Applicant: TRUSTEES OF BOSTON COLLEGE, Chestnut Hill, MA (US)

(72) Inventors: Jianmin Gao, Newton, MA (US); Hong Zheng, Brighton, MA (US)

(73) Assignee: TRUSTEES OF BOSTON COLLEGE, Chestnut Hill, MA (US)

( * ) Notice: Subject to any disclaimer, the term of this patent is extended or adjusted under 35 U.S.C. 154(b) by 0 days.

(21) Appl. No.: 13/886,549

(22) Filed: May 3, 2013

(65) Prior Publication Data

US 2013/0315836 A1 Nov. 28, 2013

Related U.S. Application Data

(60) Provisional application No. 61/642,678, filed on May 4, 2012.

(51) Int. Cl.

| | |
|---|---|
| A61K 49/00 | (2006.01) |
| G01N 21/64 | (2006.01) |
| G01N 33/58 | (2006.01) |
| G01N 33/50 | (2006.01) |
| G01N 33/52 | (2006.01) |

(52) U.S. Cl.
CPC ........ *A61K 49/0041* (2013.01); *G01N 21/6486* (2013.01); *G01N 33/5005* (2013.01); *G01N 33/52* (2013.01); *G01N 33/582* (2013.01); *G01N 2800/52* (2013.01); *G01N 2800/7028* (2013.01)

(58) Field of Classification Search
CPC ..... A61K 49/00; G01N 33/582; G01N 33/52; G01N 33/5005
USPC ........ 535/4, 6, 15, 183, 193, 320.1, 325, 350; 424/9.6, 9.341, 9.1, 1.49
See application file for complete search history.

(56) References Cited

PUBLICATIONS

Olga Burchak et al. Fluorescein-based amino acids for solid phase synthesis of fluorogenci protease substrates, Bioorganic and Med. Chem. 2006, 14, 2559-2568.*
Oliver Kepp et al. Cell death assays for drug discovery, Nature Reviews, vol. 10, 221-237, 2011.*
Ana Gomes et al. Fluorescence probes used for detection of reactive oxygen species, J. Biochem. Biophys. Methods, 65, 45-80, 2005.*
Burtea, C. et al., Mol. Pharm., 6:1903-1919 (2009). "Peptidic targeting of phosphatidylserine for the MRI detection of apoptosis in atherosclerotic plaques."
Edgington, L.E. et al., Nat. Med., 15:967-973 (2009). "Noninvasive optical imaging of apoptosis by caspase-targeted activity-based probes."
Hanshaw, R.G. et al., Bioorg Med Chem, 13:5035-5042 (2005). "New reagents for phosphatidylserine recognition and detection of apoptosis."
Hanshaw, R.G. et al., ChemBioChem, 6:2214-2220 (2005). "Fluorescent detection of apoptotic cells by using zinc coordination complexes with a selective affinity for membrane surfaces enriched with phosphatidylserine."
Johnson, L.L. et al., J. Nucl. Med., 46:1186-1193 (2005). "99mTc-annexin V imaging for in vivo detection of atherosclerotic lesions in porcine coronary arteries."
Kartachova, M. et al., J. Clin. Oncol. 25:2534-2539 (2007). "Prognostic significance of 99mTc Hynic-rh-annexin V scintigraphy during platinum-based chemotherapy in advanced lung cancer."
Kaufmann, S. H. et al., Methods, 44:262-272 (2008). "Apoptosis-associated caspase activation assays."
Kepp, O. et al., Nat Rev Drug Discov, 10:221-237 (2011). "Cell death assays for drug discovery."
Park, D. et al., J. Am. Chem. Soc., 133:2832-2835 (2011). "Noninvasive imaging of cell death using an Hsp90 ligand."
Reshef, A. et al., JNucl Med, 51:837-840 (2010). "Small-molecule biomarkers for clinical PET imaging of apoptosis."
Swairjo, M.A. et al., Nat. Struct. Biol., 2:968-974 (1995). "Ca(2+)-bridging mechanism and phospholipid head group recognition in the membrane-binding protein annexin V."
Tait, J.F., J. Nucl. Med., 49:1573-1576 (2008). "Imaging of apoptosis."
Thapa, N. et al., J Cell Mol Med, 12:1649-1660 (2008). "Discovery of a phosphatidylserine-recognizing peptide and its utility in molecular imaging of tumour apoptosis."
van Engeland, M. et al., Cytometry, 31:1-9 (1998). "Annexin V-affinity assay: a review on an apoptosis detection system based on phosphatidylserine exposure."
Zheng, H. et al., Journal of the American Chemical Society, 133:15280-15283 (2011). "Cofactor-free detection of phosphatidylserine with cyclic peptides mimicking lactadherin."
Aloya et al., "Molecular imaging of cell death in vivo by a novel small molecule probe", Apoptosis, 11:2089-2101 (2006).
Chekeni et al., "Pannexin 1 channels mediate 'find-me' signal release and membrane permeability during apoptosis", Nature, 467, 863-867 (2010).
Cohen et al., "From the Gla domain to a novel small-molecule detector of apoptosis", Cell Res, 19:625-637 (2009).
Damianovich et al., "ApoSense: a novel technology for functional molecular imaging of cell death in models of acute renal tubular necrosis", Eur J Nucl Med Mol Imaging, 33:281-291 (2006).
Idziorek et al., " YOPRO-1 permits cytofluorometric analysis of programmed cell death (apoptosis) without interfering with cell viability", J Immunol Methods, 185:249-258 (1995).

\* cited by examiner

*Primary Examiner* — Michael G Hartley
*Assistant Examiner* — Jagadishwar Samala
(74) *Attorney, Agent, or Firm* — Nixon Peabody LLP; Ronald I. Eisenstein

(57) ABSTRACT

Provided herein are compounds useful for selectively labeling an apoptotic cell, and methods and assays using such compounds for the detection of an apoptotic cell in vivo or in a biological sample obtained from a subject.

8 Claims, 13 Drawing Sheets

CELL-PENETRATING MARKERS OF APOPTOSIS

CROSS-REFERENCE TO RELATED APPLICATIONS

This application claims benefit under 35 U.S.C. §119(e) of U.S. Provisional Application No. 61/642,678 filed May 4, 2012, the contents of which are incorporated herein by reference in its entirety.

FIELD

The disclosure herein relates to the detection of apoptotic cells.

BACKGROUND

Apoptosis is a mechanism for programmed cell death that typically occurs during embryogenesis, development and during the normal physiological response to aging. Apoptosis can also be triggered in response to a cell stressor, such as heat, radiation, nutrient deprivation, viral infection, hypoxia, increased intracellular calcium concentration and in response to certain glucocorticoid receptor activation.

Apoptosis, in part, initiates activation of one or more caspase signaling pathways. Caspases are strong proteases that cleave after aspartic acid residues and once activated, are responsible for proteolytic cleavage of a broad spectrum of cellular targets that ultimately lead to cell death.

Defective apoptosis regulation can lead to a variety of disorders. For example, impaired apoptotic activity can lead to inappropriate cell survival, and is associated with tumor growth, cancer, autoimmune disease, and inflammatory disease. Conversely, pathologically high levels of apoptosis can result in abnormal initiation of cell death pathways, as observed in e.g., neurodegenerative diseases (e.g., Parkinson's disease, Alzheimer's disease, dementia, and cerebral ischemia, among others) and infection (e.g., AIDS).

SUMMARY

Provided herein are compounds useful for selectively labeling an apoptotic cell, and methods and assays using such compounds for the detection of an apoptotic cell in vivo or in a biological sample obtained from a subject. The methods and assays described herein can be used to diagnose a disease or disorder associated with dysregulated apoptosis, for example, cancer or autoimmune disease, among others. In addition, the methods and assays described herein can be used to monitor treatment of a subject with an agent expected to modulate an apoptotic pathway, such as monitoring treatment of a subject with an anti-cancer agent.

In one aspect, provided herein is a composition of formula (I)

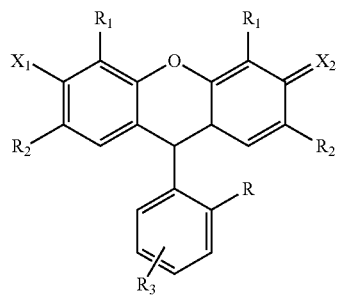

wherein $R_1$ is hydrogen, $SO_3^-$, OH, $OR_5$; COON, $COOR_5$, $NH_2$, or $N(R^B)_2$;

$X_1$ is OH, $NH_2$, $N(R_7R_8)$; $CF_3$, CN, $C(O)R^B$, $CO_2R^B$, $C(O)N(R^B)_2$, $OR^B$, $N(R^B)_2$, N=C=S, $NHC(O)R^B$, $NHC(O)OR^B$, $NHC(S)R^B$, $NHC(S)N(R^B)_2$, $NHSO_2R^B$, $NHSO_2N(R^B)_2$, $NO_2$, $N_2$—$R^B$, $SOR^B$, $SO_2R^B$, $SO_3R^B$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

$X_2$ is O, $NH_2$, or $N(R_7R_8)$;

each $R_2$ is independently hydrogen, halogen, $CF_3$, alkyl, OH, or taken together with either $X_1$ or $X_2$ forms optionally substituted carbocyclic, optionally substituted heterocyclic, optionally substituted aryl, or optionally substituted heteroaryl;

$R_3$ is $C(O)R_4$, or $N(H)R_4$;

$R_4$ is hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^B$; OH; $OR^B$; —$NH(R^B)$, —$N(R^B)_2$, —C(=O)NH($R^B$); —C(=O)N($R^B$)$_2$; —C(=S)NH($R^B$); —C(=S)N($R^B$)$_2$;

each $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_5$ is a protecting group; aliphatic; heteroaliphatic; acyl; aryl moiety; or heteroaryl; and each $R_7$ and $R_8$ is independently hydrogen, or alkyl;

R is hydrogen, $C_{1-6}$alkyl, or $COOR_9$;

$R_9$ is hydrogen, or $C_{1-4}$alkyl.

In one embodiment, the compound of Formula (I) or Formula (Ia), is a fluorescein derivative wherein the benzoic acid is substituted with $R_3$. In some embodiments, the fluorescein derivative is an Alexa-dye derived from xanthene. In some embodiments, the Alexa-dye derived from xanthene is Alexa Fluor 488, 514, 532, 546, 568, 594, or 610.

In one embodiment, the compound of Formula (I) is Formula (IIa)

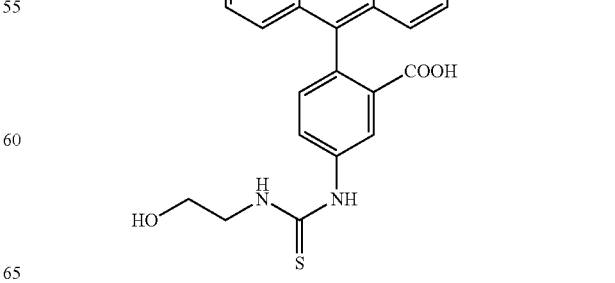

In another embodiment, the compound of Formula (I) is Formula (IIIa) or (IIIb)

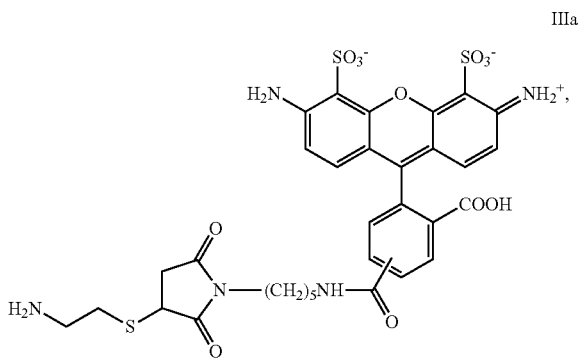
IIIa

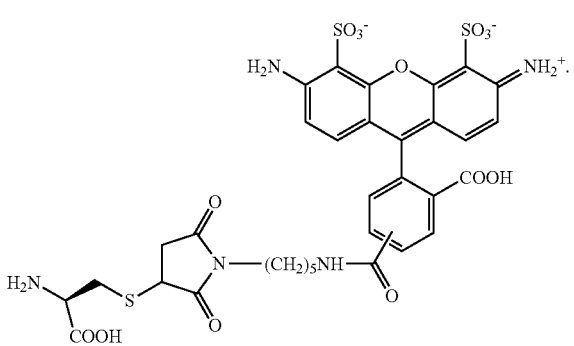
IIIb

In some embodiments, the compound of formula (IIIa) is the compound of formula (IIIa1):

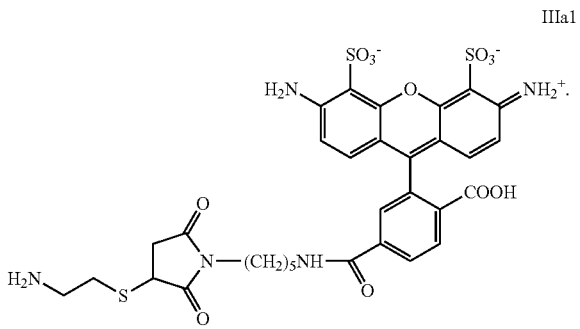
IIIa1

In some embodiments, the compound of formula (IIIa) is the compound of formula (IIIa2):

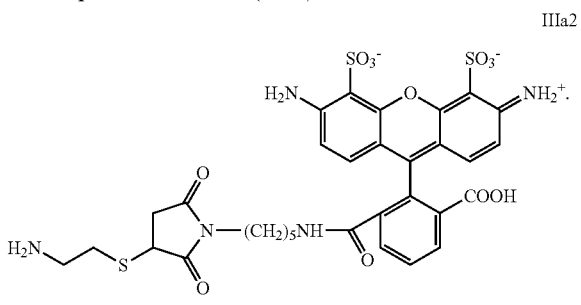
IIIa2

In some embodiments, the compound of formula (IIIa) is a mixture of formula (IIIa1) and (IIIa2).

In some embodiments, the compound of formula (IIIb) is the compound of formula (IIIb1):

IIIb1

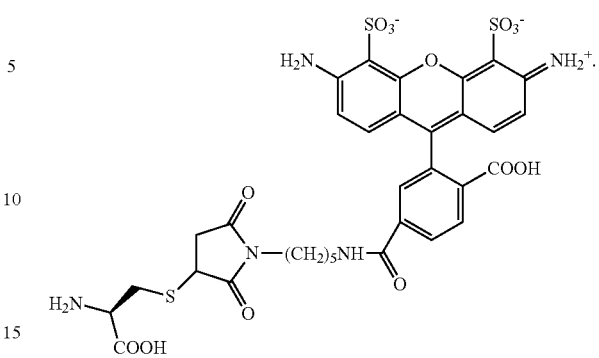

In some embodiments, the compound of formula (IIIb) is the compound of formula (IIIb2):

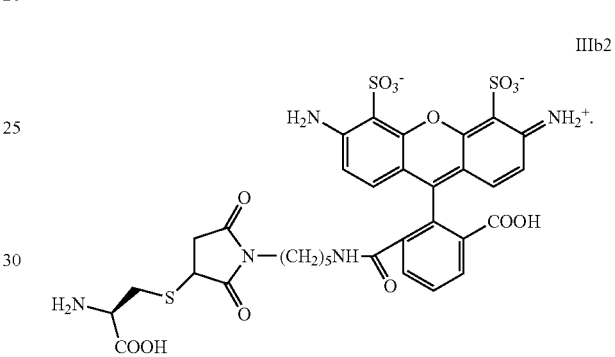
IIIb2

In some embodiments, the compound of formula (IIIb) is a mixture of formula (IIIb1) and (IIIb2).

Another aspect provided herein relates to assays for detecting apoptosis in a biological sample comprising a cell, the method comprising: analyzing a biological sample comprising a cell for the presence of a fluorescent cell, wherein the biological sample was contacted with a fluorescent compound of formula (I), wherein the presence of a fluorescent cell permits detection of apoptosis in the biological sample.

In one embodiment of the assays described herein, the compound of Formula (I) is selected from the group consisting of Formula (IIa), (IIIa), and (IIIb).

In another embodiment of the assays described herein, the biological sample is obtained from a subject.

In another embodiment of the assays described herein, the biological sample is contacted with the fluorescent compound in vitro.

In another embodiment of the assays described herein, the assay does not detectably label a non-apoptotic cell.

In another embodiment of the assays described herein, the biological sample is a tumor sample, a biopsy sample, a tissue sample, a blood sample, a cell culture sample, or a tissue culture sample.

In another embodiment of the assays described herein, the biological sample remains in situ or in vivo.

In another embodiment of the assays described herein, the fluorescent compound is administered to the subject.

In another embodiment of the assays described herein, the subject has a tumor or a cancer.

In another embodiment of the assays described herein, the subject is currently undergoing treatment with an anti-cancer agent.

In another embodiment of the assays described herein, the subject was previously treated with an anti-cancer agent.

In another embodiment of the assays described herein, the step of detecting a fluorescent cell is performed using fluorescence assisted cell sorting (FACS), flow cytometry, immunocytochemistry, confocal microscopy, fluorescent microscopy, positron emission tomography, or single photon emission computed tomography.

In another embodiment of the assays described herein, the step of detecting a fluorescent cell is performed using a biological sample obtained at two or more time points from the same subject.

In another embodiment of the assays described herein, the two or more time points are separated by hours, days, weeks, months or years.

Another aspect provided herein relates to an assay for monitoring treatment with an anti-cancer agent: the assay comprising: (a) analyzing a biological sample comprising a cell for the presence of a fluorescent cell at a first time point, wherein the biological sample is from a subject being treated with an anti-cancer agent, and wherein the biological sample was contacted with a fluorescent compound of Formula (I), and (b) comparing the number or percentage of fluorescent cells detected at the first time point compared to a reference sample, wherein an increase in the number or percentage of fluorescent cells in the biological sample compared to the reference sample indicates that the treatment of the subject with an anti-cancer agent is, or continues to be, effective.

In one embodiment of the assays described herein, the compound of Formula (I) is selected from the group consisting of Formula (IIa), (IIIa), and (IIIb).

In another embodiment of the assays described herein, the biological sample comprising a cell is obtained from a subject.

In another embodiment of the assays described herein, the biological sample is contacted with the fluorescent compound in vitro.

In another embodiment of the assays described herein, the assay does not detectably label a non-apoptotic cell.

In another embodiment of the assays described herein, the biological sample is a tumor sample, a biopsy sample, a tissue sample, a blood sample, a cell culture sample, or a tissue culture sample.

In another embodiment of the assays described herein, the biological sample is an in situ or in vivo biological sample.

In another embodiment of the assays described herein, the fluorescent compound is administered to the subject.

In another embodiment of the assays described herein, the step of detecting a fluorescent cell is performed using fluorescence assisted cell sorting (FACS), flow cytometry, immunocytochemistry, confocal microscopy, fluorescent microscopy, positron emission tomography, or single photon emission computed tomography.

In another embodiment of the assays described herein, the reference sample comprises a biological sample comprising a cell from a subject at a second time point.

In another embodiment of the assays described herein, the second time point is after the first time point.

In another embodiment of the assays described herein, the two or more time points are separated by hours, days, weeks, months or years.

In another embodiment of the assays described herein, the reference sample is a value or range of values.

In another embodiment of the assays described herein, the value or range of values is obtained from a plurality of subjects in a population.

In another embodiment of the assays described herein, the plurality of subjects in a population are treated with an anti-cancer agent.

In another embodiment of the assays described herein, the plurality of subjects in a population have not been treated with an anti-cancer agent.

Another aspect provided herein relates to a method of detecting apoptosis in a biological sample, the method comprising: detecting the presence of a fluorescent cell in a biological sample contacted with a fluorescent compound of Formula (I), wherein the biological sample comprises a cell, and wherein the presence of a fluorescent cell detects apoptosis in the biological sample.

In one embodiment of the methods described herein, the compound of Formula (I) is selected from the group consisting of Formula (IIa), (IIIa), and (IIIb).

In another embodiment of the methods described herein, the biological sample is obtained from a subject.

In another embodiment of the methods described herein, the biological sample is contacted with the fluorescent compound in vitro.

In another embodiment of the methods described herein, the fluorescent compound of Formula (I) does not detectably label a non-apoptotic cell.

In another embodiment of the methods described herein, the biological sample is a tumor sample, a biopsy sample, a tissue sample, a blood sample, a cell culture sample, or a tissue culture sample.

In another embodiment of the methods described herein, the biological sample is an in situ or in vivo biological sample.

In another embodiment of the methods described herein, the fluorescent compound is administered to the subject.

In another embodiment of the methods described herein, the subject has a tumor, or a cancer.

In another embodiment of the methods described herein, the subject is currently undergoing treatment with an anti-cancer agent.

In another embodiment of the methods described herein, the subject was previously treated with an anti-cancer agent.

In another embodiment of the methods described herein, the step of detecting the presence of a fluorescent cell is performed using fluorescence assisted cell sorting (FACS), flow cytometry, immunocytochemistry, confocal microscopy, fluorescent microscopy, positron emission tomography, or single photon emission computed tomography.

In another embodiment of the methods described herein, the step of detecting the presence of a fluorescent cell is performed at two or more time points from the same subject.

In another embodiment of the methods described herein, the two or more time points are separated by hours, days, weeks, months or years.

Another aspect provided herein relates to methods for monitoring treatment with an anti-cancer agent: the method comprising: (a) detecting the presence of a fluorescent cell in a biological sample comprising a cell at a first time point, wherein the biological sample is from a subject being treated with an anti-cancer agent, and wherein the biological sample was contacted with a fluorescent compound of Formula (I), and (b) comparing the number or percentage of fluorescent cells detected at the first time point compared to a reference sample, wherein an increase in the number or percentage of fluorescent cells in the biological sample compared to the reference sample indicates that the treatment of the subject with an anti-cancer agent is, or continues to be, effective.

In another embodiment of the methods described herein, the compound of Formula (I) is selected from the group consisting of Formula (IIa), (IIIa), and (IIIb).

In another embodiment of the methods described herein, the biological sample comprising a cell is obtained from a subject.

In another embodiment of the methods described herein, the reference sample comprises a biological sample comprising a cell from a subject at a second time point.

In another embodiment of the methods described herein, the second time point is after the first time point.

In another embodiment of the methods described herein, the two or more time points are separated by hours, days, weeks, months or years.

In another embodiment of the methods described herein, the reference sample is a value or range of values.

In another embodiment of the methods described herein, the value or range of values is obtained from a plurality of subjects in a population.

In another embodiment of the methods described herein, the plurality of subjects in a population are treated with an anti-cancer agent.

In another embodiment of the methods described herein, the plurality of subjects in a population have not been treated with an anti-cancer agent.

In another embodiment of the methods described herein, the biological sample is contacted with the fluorescent compound in vitro.

In another embodiment of the methods described herein, the fluorescent compound of Formula (I) does not detectably label a non-apoptotic cell.

In another embodiment of the methods described herein, the biological sample is a tumor sample, a biopsy sample, a tissue sample, a blood sample, a cell culture sample, or a tissue culture sample.

In another embodiment of the methods described herein, the biological sample is an in situ or in vivo biological sample of a subject.

In another embodiment of the methods described herein, the fluorescent compound is administered to the subject.

In another embodiment of the methods described herein, detecting a fluorescent cell is performed using fluorescence assisted cell sorting (FACS), flow cytometry, immunocytochemistry, confocal microscopy, fluorescent microscopy, positron emission tomography, or single photon emission computed tomography.

Another aspect provided herein relates to kits for labeling an apoptotic cell, the kit comprising: (a) a fluorescent compound of Formula (I); and (b) instructions for using the fluorescent compound to label an apoptotic cell.

In one embodiment of the kits described herein, the kit further comprises a positive control and/or a negative control.

In another embodiment of the kits described herein, the compound of Formula (I) is selected from the group consisting of Formula (IIa), (IIIa), and (IIIb).

BRIEF DESCRIPTION OF THE DRAWINGS

FIG. 2A shows flow cytometry analysis of Jurkat cells in the presence of F1-EA and AV-PE (x-axis: the FITC channel; y-axis: the PE channel). FIG. 2B shows a representative confocal image of AV-PE fluorescence.

FIG. 2C shows a representative confocal image of F1-EA fluorescence. FIG. 2D shows an overlay of the images from FIGS. 2B and 2C.

FIG. 3A depicts a collection of structures that selectively penetrate apoptotic cells membranes. FIG. 3B depicts a comparison of Alexa-Cysteamine and Alexa-peptides indicating molecular size as a determining factor for apoptotic cell entry. The flow cytometry results: left column, Jurkat cells with CPT treatment; right column, Jurkat cells without CPT treatment.

FIGS. 5A and 5C display the FITC channel; FIGS. 5B and 5D display the phase contrast channel. FIGS. 5A and 5B are F1-EA stained, CPT treated cell samples and indicate apoptotic cells (bright spots) inside which F1-EA is accumulated, the dark hollows are evidence for healthy cells blocking F1-EA from entering the cell; FIGS. 5C and 5D are CPT untreated cell samples stained with F1-EA, where only dark hollows were observed.

FIG. 6A shows fluorescein stained, CPT treated cell samples, with almost all cells displaying low intensity fluorescence, indicating that a small amount of dye was inside the cell. FIG. 6B shows F1-EA stained, CPT treated cell samples, where part of the cell population is significantly brighter than others indicating selective staining FIG. 6C shows CPT untreated cell samples stained with fluorescein; the staining pattern is very similar to the CPT treated samples, indicating there is no selectivity for fluorescein to penetrate through apoptotic cells membranes. FIG. 6D shows CPT untreated cell samples stained with F1-EA showing no staining but only dark hollow areas observed at all cell positions, indicating F1-EA cannot enter healthy cells.

FIGS. 8A and 8B show Rhodamine B stained cells while FIGS. 8C and 8D show Rd-EA stained cells. FIGS. 8A and 8C are CPT treated cells while FIGS. 8B and 8D are CPT untreated cells.

DETAILED DESCRIPTION

Figure 1A:
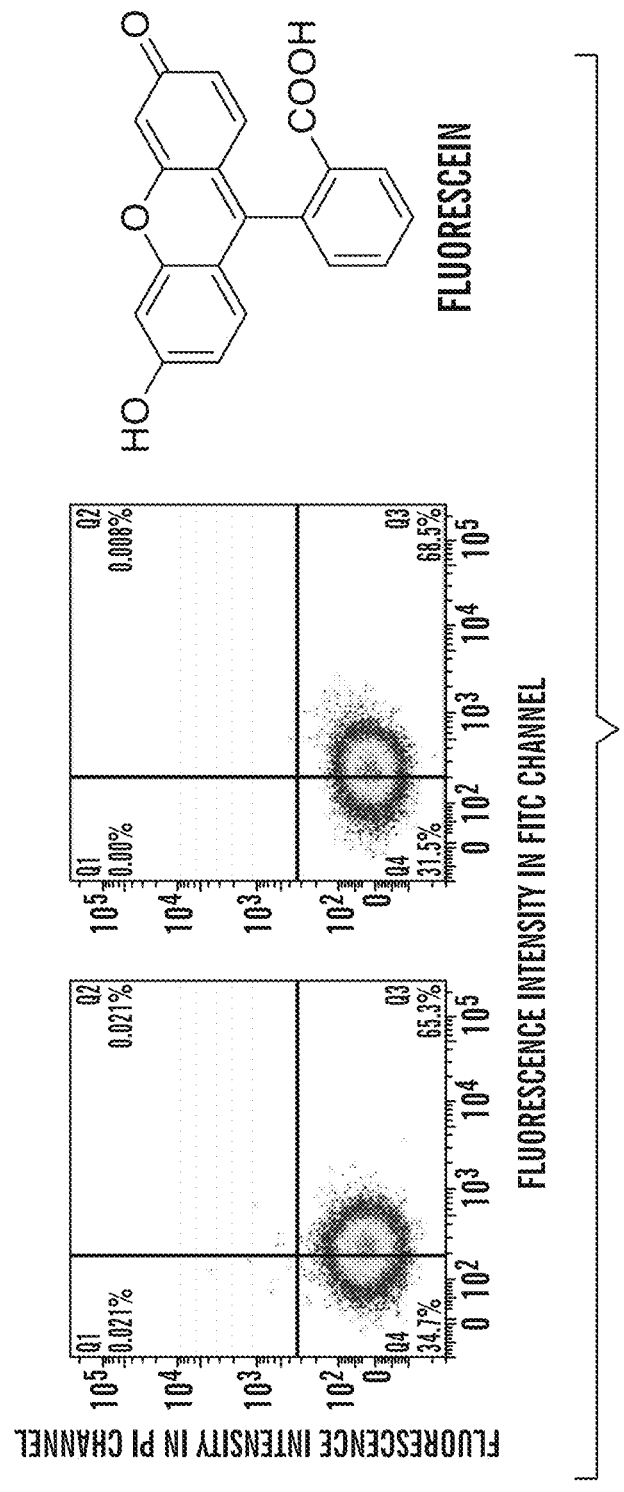
FIGS. 1A-1C are graphs depicting flow cytometry analysis of fluorescein (FIG. 1A) and the derivative F1-EA (FIG. 1B). FITC labeled Annexin V (AV-FITC) was used as a positive control (FIG. 1C). Jurkat cells with (left panel) and without (right panel) CPT treatment were stained with the three agents respectively. x-axis: the FITC channel; y-axis: the PI (propidium iodide channel).

Provided herein are compositions containing one or more compounds that selectively enter apoptotic cells, but do not enter non-apoptotic cells, thereby permitting selective labeling of an apoptotic cell, for example, in a biological sample of a subject. Such compositions can be used to diagnose a disease or disorder associated with dysregulated apoptosis, and further can be used to monitor treatment using an agent known to modulate an apoptotic pathway (e.g., an anti-cancer agent).

Definitions

The terms "subject" and "individual" are used interchangeably herein, and refer to an animal, for example, a human from whom biological samples for use with the compositions and assays described herein can be obtained. For those conditions or disease states that are specific for a certain animal such as a human subject, the term subject refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, typically the subject is a mammal such as a human, or other mammals such as a domesticated mammal, e.g., dog, cat, horse, and the like, or production mammal, e.g., cow, sheep, pig, and the like. In one embodiment, the subject is a human.

A "cancer" or "tumor," as used herein, refers to an uncontrolled growth of cells which can interfere with the normal functioning of bodily organs and/or systems. A subject that has a cancer or a tumor is a subject having objectively measurable cancer cell(s) present in the subject's body. Included in this definition are benign and malignant cancers, as well as dormant tumors or micrometastases.

By "metastasis" is meant the spread of cancer from its primary site to other places in the body. For example, cancer cells can break away from a primary tumor, penetrate into lymphatic and blood vessels, circulate through the bloodstream, and grow in a distant focus (metastasize) in normal tissues elsewhere in the body.

The term "anti-cancer agent" or "cancer therapy" refers to an agent useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR) antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

The practice of the methods described herein will employ, unless otherwise indicated, conventional techniques of molecular biology, microbiology and recombinant DNA techniques, which are within the abilities of one of skill in the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Polynucleotide Hybridization (B. D. Harms & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). The practice of the methods described herein can also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456; 5,246,577; 5,126,025; 5,364,521; 4,985,129; as well as in U.S. patent application Ser. Nos. 10/113,034; 10/387,286; 10/719,185; 10/600,201; 10/752,123 and 10/719,746.

The term "isomer" as used herein refers to a compound with the same molecular formula but different structural formulas. Isomers do not necessarily share similar properties, unless they also have the same functional groups. There are many different classes of isomers, like stereoisomers, enantiomers, geometrical isomers, etc. There are two main forms of isomerism: structural isomerism and stereoisomerism (spatial isomerism).

The designations "R" and "S" are used to denote the absolute configuration of a molecule about its chiral center. The designations may appear as a prefix or as a suffix; they may or may not be separated from the isomer by a hyphen; they may or may not be hyphenated; and they may or may not be surrounded by parentheses.

The term "S isomer" as used herein refers to an enantiomer with the chiral center S according to a system by which its substituents are each assigned a priority, according to the Cahn-Ingold-Prelog priority rules (CIP), based on atomic number, where the priority of atomic number decreases in counterclockwise direction, it is S enantiomer (from the Latin Sinestra, meaning "left"). Without wishing to be limited to theory, if the center is oriented so that the lowest-priority of the four is pointed away from a viewer, the viewer will then see two possibilities: If the priority of the remaining three substituents decreases in clockwise direction, it is labeled R (from the Latin Rectus, meaning "right"), if it decreases in counterclockwise direction, it is S (from the Latin Sinestra, meaning "left").

The term "prodrug" refers to a compound that is formulated as a precursor compound that, following administration, activates or releases the active component of the compound in vivo via a chemical or physiological process (e.g., upon being brought to physiological pH or through enzyme activity). A discussion of the synthesis and use of prodrugs is provided by Higuchi and Stella, Prodrugs as Novel Delivery Systems, vol. 14 of the ACS Symposium Series, and Bioreversible Carriers in Drug Design, ed. Edward B. Roche, American Pharmaceutical Association and Pergamon Press, 1987. Accordingly, the term "prodrug" refers to compounds that can be converted via some chemical or physiological process (e.g., enzymatic processes and metabolic hydrolysis) to an inactive form that can be activated in vivo by some co-compound or a specific environmental condition, e.g., pH etc. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject.

The term "therapeutically effective amount" as used herein refers to an amount sufficient to achieve a beneficial or desired clinical result upon treatment. Specifically, the term "therapeutically effective amount" means an amount of a compound as described herein that is sufficient to detect an apoptotic cell in a biological sample, as that term is used herein. The term "therapeutically effective amount" can also refer to the amount of a therapeutic agent (e.g., an anti-cancer agent) that reduces at least one symptom of a disease or disorder to be treated (e.g., cancer, autoimmune disease etc.), for example, by at least 10%. Therapeutically effective amounts will vary, as recognized by those skilled in the art, depending on the specific disease treated, the route of administration, the excipient selected, and the possibility of combination therapy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

Physiological effects of a compound as disclosed herein on the subject can be measured to determine the therapeutically effective amount include, without limitation, levels of apoptotic cells, tumor shrinkage, reduction in at least one symptom of disease, reduction in need for hospitalizations or medical interventions etc. In one embodiment, the physiological effect of a therapeutic compound is monitored by detecting and/or quantifying the number or percentage of apoptotic cells in a biological sample, using e.g. the methods and assays described herein.

As used herein, the terms "alkyl," "alkenyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylalcohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, thiazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The aryl, and heteroaryl groups can be unsubstituted or substituted by one or more substituents independently selected from the group consisting of alkyl, alkoxy, methylenedioxy, ethylenedioxy, alkylthio, haloalkyl, haoalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylhio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

The term "arylalkyl," as used herein, refers to a group comprising an aryl group attached to the parent molecular moiety through an alkyl group.

The term "carbonyl," as used herein, refers to "C(=O)".

As used herein, the term "cyclyl" refers to a nonaromatic 5-8 membered monocyclic, 8-12 membered bicyclic, or 11-14 membered tricyclic ring system, which can be saturated or partially unsaturated. Representative saturated cyclyl groups include, but are not limited to, cyclopropyl, cyclobutyl, cyclopentyl, cyclopentenyl, cyclohexyl, cyclohexenyl, cycloheptyl, cyclooctyl, and the like; while unsaturated cyclyl groups include cyclopentenyl and cyclohexenyl, and the like.

As used herein, the term "aryl" refers to an aromatic 5-8 membered monocyclic, 8-12 membered bicyclic, or 11-14 membered tricyclic ring system. Examples of aryl groups include phenyl, naphthyl and the like.

As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, thiazolyl, benzimidazolyl, pyrimidinyl, thiophenyl or thienyl, quinolinyl, indolyl, oxazolyl, and the like.

As used herein, the term "halogen" refers to iodine, bromine, chlorine, and fluorine.

As used herein, the terms "optionally substituted alkyl," "optionally substituted cyclyl," "optionally substituted heterocyclyl," "optionally substituted aryl," and "optionally substituted heteroaryl" means that, when substituted, at least one hydrogen atom in said alkyl, cyclyl, heterocylcyl, aryl, or heteroaryl is replaced with a substituent. In the case of an oxo substituent (=O) two hydrogen atoms are replaced. In this regard, substituents include oxo, halogen, alkyl, cyclyl, heterocyclyl, aryl, heteroaryl, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl, cyclyl, heterocyclyl, aryl or heterocycle, and each of said alkyl, cyclyl, heterocyclyl, aryl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

The terms "acyl," "carboxyl group," or "carbonyl group" are recognized in the art and can include such moieties as can be represented by the general formula:

wherein W is OR$^w$, N(R$^w$)$_2$, SR$^w$, or R$^w$, R$^w$ being hydrogen, alkyl, heteroalkyl, alkenyl, heteroalkenyl, alkynyl, heteroalkynyl, aryl, heteroaryl, heterocycle, substituted derivatives thereof, or a salt thereof. For example, when W is O-alkyl, the formula represents an "ester," and when W is OH, the formula represents a "carboxylic acid." When W is alkyl, the formula represents a "ketone" group, and when W is hydrogen, the formula represents an "aldehyde" group. Those of ordinary skill in the art will understand the use of such terms.

As used herein, the term "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. The heterocycle can include portions which are saturated or unsaturated. In some embodiments, the heterocycle may include two or more rings (e.g., cycloalkyls, cycloalkenyls, cycloalkynyls, aryls and/or heterocyclyls) in which two or more carbons are common to two adjoining rings, e.g., the rings are "fused rings." In some embodiments, the heterocycle may be a "bridged" ring, where rings are joined through non-adjacent atoms, e.g., three or more atoms are common to both rings. Each of the rings of the heterocycle may be optionally substituted. Examples of heterocyclyl groups include, for example, piperazinyl, pyrrolidinyl, dioxanyl, morpholinyl, tetrahydrofuranyl thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with substituents including, for example, halogen, aryl, heteroaryl, alkyl, heteroalkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, CF$_3$, CN, or the like.

As used herein, the term "substituted" is contemplated to include all permissible substituents of organic compounds, "permissible" being in the context of the chemical rules of valence known to those of ordinary skill in the art. In some cases, "substituted" refers to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic, fused, and bridged substituents of organic compounds. Illustrative substituents include, for example, those described herein. The permissible substituents can be one or more and the same or different for appropriate organic compounds. It is contemplated herein that heteroatoms such as nitrogen may have hydrogen substituents and/or any permissible substituents of organic compounds described herein which satisfy the valencies of the heteroatoms. This description is not intended to be limited in any manner by the permissible substituents of organic compounds.

The term "pharmaceutically acceptable excipient," as used herein, refers to carriers and vehicles that are compatible with the active ingredient (for example, a compound as described herein) of a pharmaceutical composition as described herein (and preferably capable of stabilizing it) and not deleterious to the subject to be treated. For example, solubilizing agents that form specific, more soluble complexes with the compounds as described herein can be utilized as pharmaceutical excipients for delivery of the compounds. Suitable carriers and vehicles are known to those of ordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions described herein can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds described herein.

The terms "salts" and "pharmaceutically acceptable salts" refer to organic and inorganic salts of a compound, a stereoisomer of a compound, or a prodrug of a compound as disclosed herein. Thus, as used herein, the term "pharmaceutically acceptable salt," is a salt formed from an acid and a basic group of a compound as described herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound as disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that the methods and assays described herein are not limited to the particular methodology, protocols, and reagents, etc., described herein and as such can vary. The terminology used herein is for the purpose of describing particular embodiments only, and is not intended to limit the scope of the present description, which is defined solely by the claims.

All patents and other publications identified herein, both supra and infra, are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Cell Penetrating Compounds

In one aspect, provided herein is a composition of formula (I)

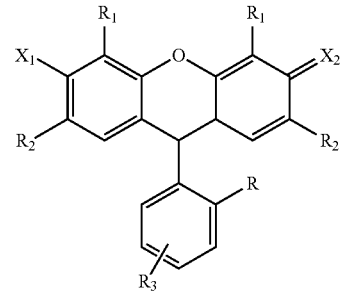

wherein $R_1$ is hydrogen, $SO_3^-$, OH, $OR_5$; COOH, $COOR_5$, $NH_2$, or $N(R^B)_2$;

$X_1$ is OH, $NH_2$, $N(R_7R_8)$; $CF_3$, CN, $C(O)R^B$, $CO_2R^B$, $C(O)N(R^B)_2$, $OR^B$, $N(R^B)_2$, N=C=S, $NHC(O)R^B$, $NHC(O)OR^B$, $NHC(S)R^B$, $NHC(S)N(R^B)_2$, $NHSO_2R^B$, $NHSO_2N(R^B)_2$, $NO_2$, $N_2$—$R^B$, $SOR^B$, $SO_2R^B$, $SO_3R^B$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

$X_2$ is O, $NH_2$, or $N(R_7R_8)$;

each $R_2$ is independently hydrogen, halogen, $CF_3$, alkyl, OH, or taken together with either $X_1$ or $X_2$ forms optionally substituted carbocyclic, optionally substituted heterocyclic, optionally substituted aryl, or optionally substituted heteroaryl;

$R_3$ is $C(O)R_4$, or $N(H)R_4$;

$R_4$ is hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^B$; OH; $OR^B$; —$NH(R^B)$, —$N(R^B)_2$, —C(=O)NH($R^B$); —C(=O)N($R^B$)$_2$; —C(=S)NH($R^B$); —C(=S)N($R^B$)$_2$;

each $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_5$ is a protecting group; aliphatic; heteroaliphatic; acyl; aryl moiety; or heteroaryl; and each $R_7$ and $R_8$ is independently hydrogen, or alkyl;

R is hydrogen, $C_{1-6}$alkyl, or $COOR_9$;

$R_9$ is hydrogen, or $C_{1-4}$alkyl.

In one embodiment, the compound of Formula (I) or Formula (Ia), is a fluorescein derivative wherein the benzoic acid is substituted with $R_3$. In some embodiments, the fluorescein derivative is an Alexa-dye derived from xanthene. In some embodiments, the Alexa-dye derived from xanthene is Alexa Fluor 488, 514, 532, 546, 568, 594, or 610.

In some embodiments, R is hydrogen. In some embodiments, R is $C_{1-6}$alkyl. In some embodiments, R is methyl, ethyl, iso-propyl, n-propyl, iso-butyl, n-butyl, tert-butyl. In some embodiments, R is COOR$_9$. In some embodiments, R$_9$ is hydrogen. In some embodiments, R$_9$ is C$_{1-4}$alkyl.

In some embodiments, at least on R$_1$ is hydrogen. In some embodiments, both R$_1$ are hydrogen. In some embodiments, at least one R$_1$ is SO$_2$. In some embodiments, at least one R$_1$ is SO$_3^-$. In some embodiments, both R$_1$ are SO$_3^-$. In some embodiments each R$_1$ are different. In some embodiments, both R$_1$ are the same.

In some embodiments, X$_1$ is OH. In some embodiments, X$_1$ is OR$_5$. In some embodiments R$_5$ is a protecting group. In some embodiments, R$_5$ is C$_{1-4}$alkyl. In some embodiment, X$_1$ is NH$_2$. In some embodiments, X$_1$ is N(R$_7$R$_8$). In some embodiments, R$_7$ and R$_8$ are the same. In some embodiments, R$_7$ and R$_8$ are different. In some embodiments, at least R$_7$ or R$_8$ is hydrogen. In some embodiments, at least R$_7$ or R$_8$ is C$_{1-4}$alkyl.

In some embodiments, X$_2$ is O. In some embodiment, X$_2$ is NH$_2$. In some embodiments, X$_2$ is N(R$_7$R$_8$). In some embodiments, R$_7$ and R$_8$ are the same. In some embodiments, R$_7$ and R$_8$ are different. In some embodiments, at least R$_7$ or R$_8$ is hydrogen. In some embodiments, at least R$_7$ or R$_8$ is C$_{1-4}$alkyl.

In some embodiments, both R$_2$ are the same. In same embodiments, each R$_2$ is different. In some embodiments, at least one R$_2$ is hydrogen. In some embodiments, at least one R$_2$ is halogen. In some embodiments, halogen is F, Cl, Br, I. In some embodiments, at least one R$_2$ is CF$_3$. In some embodiments, at least one R$_2$ is C$_{1-4}$alkyl. In some embodiments, at least one R$_2$ is OH.

In some embodiments, at least one R$_2$ is taken together with either X$_1$ or X$_2$ to form a cyclic system. In some embodiments, the cyclic system is optionally substituted carbocyclic system. In some embodiments, the cyclic system is optionally substituted heterocyclic system. In some embodiments, the cyclic system is optionally substituted aryl. In some embodiments, the cyclic system is optionally substituted heteroaryl. In some embodiments, the heterocyclic or heteroaryl comprises at least one N. In some embodiments, R$_2$ taken together with either X$_1$ or X$_2$ forms optionally substituted piperidine. In some embodiments, R$_2$ taken together with either X$_1$ or X$_2$ forms optionally substituted tetrahydropyridine.

In some embodiments, R$_3$ is C(O)R$_4$. In some embodiments, R$_3$ is N(H)R$_4$. In some embodiments, R$_3$ is at the ortho position. In some embodiments, R$_3$ is at the meta positions. In some embodiments, R$_3$ is at the para position.

In some embodiments, R$_4$ is a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo. In some embodiments R$_4$ is —NH(R$^B$), —N(R$^B$)$_2$; —C(=O)NH(R$^B$); —C(=O)N(R$^B$)$_2$; —C(=S)NH(R$^B$); —C(=S)N(R$^B$)$_2$; each R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo.

In some embodiments, R$_4$ is —C(S)N(H)R$_6$. In some embodiments, R$_4$ is —C(O)N(H)R$_6$.

In some embodiments, R$_6$ contains between 1 and 60 atoms. In some embodiments, R$_6$ contains between 1 and 50 atoms. In some embodiments, R$_6$ contains between 1 and 40 atoms. In some embodiments, R$_6$ contains between 1 and 30 atoms. In some embodiments, R$_6$ contains between 1 and 20 atoms. In some embodiments, R$_6$ contains between 5 and 40 atoms. In some embodiments, R$_6$ contains between 10 and 30 atoms. In some embodiments, R$_6$ contains between 15 and 20 atoms. In some embodiments, R$_6$ is a substituted alkyl-heterocyclyl. In some embodiments, R$_6$ is substituted alkyl-pyrrolidine. In some embodiments, R$_6$ is C$_{1-4}$alkylthio substituted C$_{1-8}$alkyl-pyrrolidine. In some embodiments, R$_6$ is a substituted C$_{1-4}$alkylthio substituted C$_{1-8}$alkyl-pyrrolidine. In some embodiments, R$_6$

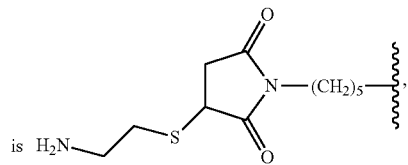

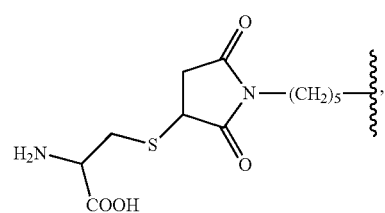

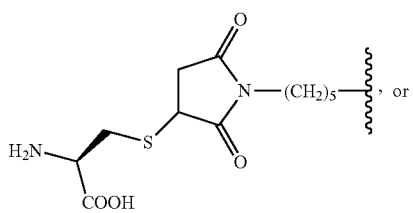

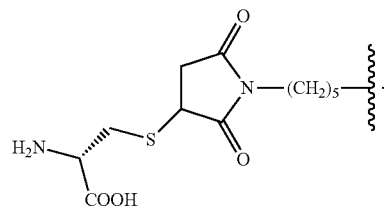

In some embodiments, the compound is of the formula (IIa)

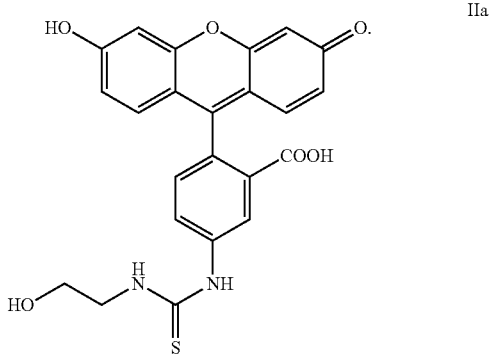 [SMILES: O=C(O)c1cc(NC(=S)NCCO)ccc1-c1c2ccc(=O)cc-2oc2cc(O)ccc12]

In some embodiments, the compound is of the formula (IIIa):

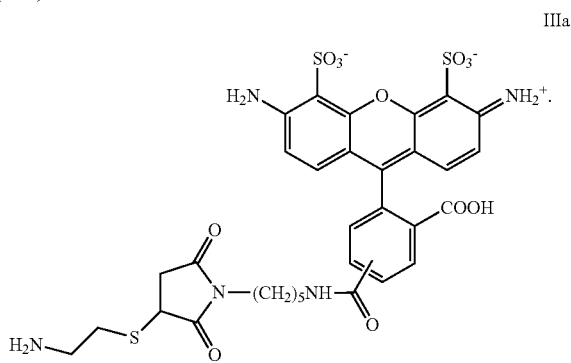

IIIa

In some embodiments, the compound of formula (IIIa) is the compound of formula (IIIa1):

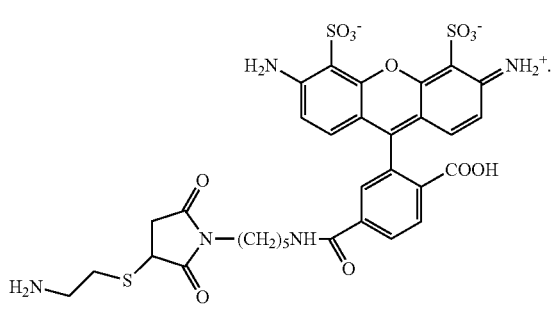

IIIa1

In some embodiments, the compound of formula (IIIa) is the compound of formula (IIIa2):

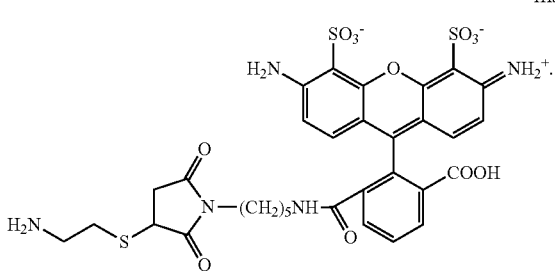

IIIa2

In some embodiments, the compound of formula (IIIa) is a mixture of formula (IIIa1) and (IIIa2).

In some embodiments, the compound is of the formula (IIIb):

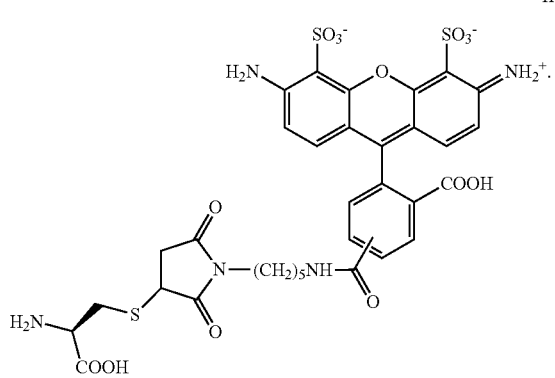

IIIb

In some embodiments, the compound of formula (IIIb) is the compound of formula (IIIb1):

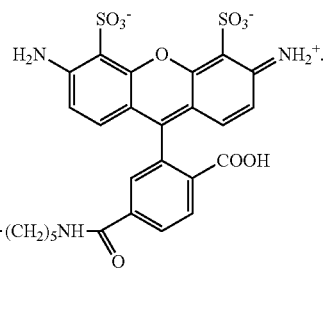

IIIb1

In some embodiments, the compound of formula (IIIb) is the compound of formula (IIIb2):

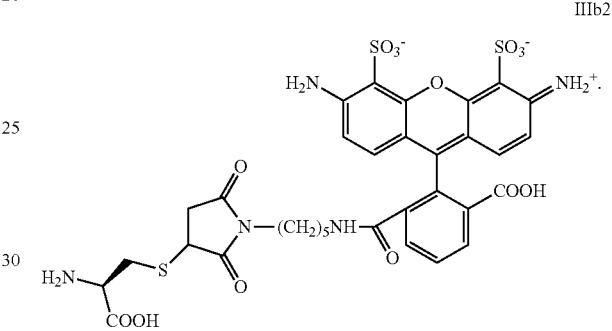

IIIb2

In some embodiments, the compound of formula (IIIb) is a mixture of formula (IIIb1) and (IIIb2).

Pharmaceutical Compositions

In one aspect as described herein, pharmaceutical compositions are provided, which comprise any one of the compounds described herein (or a prodrug, pharmaceutically acceptable salt, or other pharmaceutically acceptable form thereof), and optionally a pharmaceutically acceptable excipient. In certain embodiments, these compositions optionally further comprise one or more additional therapeutic agents. Alternatively, a compound as described herein can be administered to a patient in need thereof in combination with the administration of one or more other therapeutic agents. For example, in the treatment of cancer, one or more additional therapeutic agents for conjoint administration or inclusion in a pharmaceutical composition with a compound as described herein can be an approved chemotherapeutic agent.

For use in medicine, the salts of the compounds as described herein refer to non-toxic "pharmaceutically acceptable salts." Other salts can, however, be useful in the preparation of compounds as described herein or of their pharmaceutically acceptable salts. Suitable pharmaceutically acceptable salts of the compounds include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds as described herein carry an acidic moiety, suitable pharmaceutically acceptable salts thereof can include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which can be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (+−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

It will also be appreciated that certain compounds as described herein can exist in free form for treatment, or where appropriate, as a pharmaceutically acceptable derivative thereof. According to the compounds and assays described herein, a pharmaceutically acceptable derivative includes, but is not limited to, pharmaceutically acceptable salts, esters, salts of such esters, or a pro-drug or other adduct or derivative of a compound described herein, which upon administration to a patient in need thereof is capable of providing, directly or indirectly, a compound as otherwise described herein, or a metabolite or residue thereof.

Prodrugs and solvates of a compound as disclosed herein, such as a compound of formula (I), (IIa), (IIIa) or (IIIb), are also contemplated herein. The term "prodrug," as employed herein, denotes a compound that, upon administration to a subject, undergoes chemical conversion by metabolic or chemical processes to yield a compound described herein or a salt and/or solvate thereof.

Thus, the present description includes within its scope prodrugs of the compounds as described herein. In general, such prodrugs can be functional derivatives of the compounds which are readily convertible in vivo into the required compound. Thus, in the methods and assays described herein, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Accordingly, in some embodiments, a compound as described herein, such as a compound of any of formula (I), (IIa), (IIIa) or (IIIb) as disclosed herein can be formulated as a prodrug, and can become activated in vivo upon predefined chemical modifications. Prodrugs of an active compound as described herein, such as any compound of formula (I), (IIa), (IIIa) or (IIIb) can be prepared by modifying functional groups present in the active compound in such a way that the modifications are cleaved, either in routine manipulation or in vivo, to the parent active compound. Prodrugs of a compound as described herein, such as any compound of formula (I), (IIa), (IIIa) or (IIIb) can include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11, 345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. DrugDelivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), the content of each citation is herein incorporated by reference in its entirety.

During any of the processes for preparation of the compounds as described herein, it may be necessary and/or desirable to protect sensitive or reactive groups on any of the molecules concerned. This can be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups can be removed at a convenient subsequent stage using methods known from the art.

The compositions as described herein furthermore include all solvates of a compound as described herein, such as any compound of formula (I), (IIa), (IIIa) or (IIIb) for example hydrates, and the solvates formed with other solvents of crystallization, such as alcohols, ethers, ethyl acetate, dioxane, DMF, or a lower alkyl ketone, such as acetone, or mixtures thereof.

The compositions as described herein also include prodrug forms of a compound as described herein, such as any compound of formula (I), (IIa), (IIIa) or (IIIb), for example the alkyl esters of acids or any of the prodrugs for guanidines known to one skilled in the art. Thus, the present description includes those compounds produced in vivo after administration of a different compound (or prodrug of the compound). The in vivo effects of compounds described herein, may not be exerted by those compounds as such, but by one or more degradation products.

Various polymorphs of compounds as described herein can be prepared by crystallization of a small molecule, such as any compound of formula (I), (IIa), (IIIa) or (IIIb) under different conditions. Examples of different conditions are: using different commonly used solvents or their mixtures for crystallization; crystallization at different temperatures; and various modes of cooling, ranging from very fast to very slow cooling during crystallizations. Polymorphs can also be obtained by heating or melting the compound followed by gradual or fast cooling. The presence of polymorphs can be determined by IR spectroscopy, solid probe NMR spectroscopy, differential scanning calorimetry, powder X-ray diffraction or such other techniques.

The compounds as described herein can have asymmetric centers at any of the carbon atoms, including any one of the R substituents. Consequently, a compound as described herein, such as any compound of formula (I), (IIa), (IIIa) or (IIIb) can exist in enantiomeric or diastereomeric forms either in pure or substantially pure form or in mixtures thereof in all ratios. When diastereomeric or enantiomeric products are prepared, they can be separated by conventional methods for example, chromatographic or fractional crystallization. If mobile hydrogen atoms are present, the compositions described herein also encompass all tautomeric forms of a compound, such as any compound of formula (I), (IIa), (IIIa) or (IIIb).

The methods, assays, and compositions described herein are accordingly directed to a compound as described herein, such as any compound of formula (I), (IIa), (IIIa) or (IIIb), or a prodrug thereof, or a pharmaceutically acceptable salt of the compound, for the manufacture of a medicament for the treatment of a mammal (e.g., human) having a disease or condition associated with impaired or excessive apoptosis.

Another aspect as described herein is directed to a method for detecting apoptosis associated with e.g., cancer or an autoimmune disease, a therapeutically effective amount of a compound as described herein, such as any compound of formula (I), (IIa), (IIIa) or (IIIb), or a prodrug thereof, or a pharmaceutically, acceptable salt thereof.

As described above, the pharmaceutical compositions as described herein optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds as described herein, such as by producing any undesirable biological effect or otherwise interacting in a deleterious manner with any other component(s) of the pharmaceutical composition, its use is contemplated to be within the scope of this description. Some examples of materials which can serve as pharmaceutically acceptable excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatine; talc; excipients such as cocoa butter and suppository waxes; oils such as peanut oil, cottonseed oil; safflower oil, sesame oil; olive oil; corn oil, and soybean oil; glycols; such as propylene glycol; esters such as ethyl oleate and ethyl laurate; agar, buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories, which can be prepared by mixing the compounds described herein with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that releases the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like. The active compound(s) can also be in micro-encapsulated form with one or more excipients as noted above. In some embodiments, the solid dosage forms of the active compound can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents.

The compositions described herein encompass pharmaceutically acceptable topical formulations of compounds as described herein. The term "pharmaceutically acceptable topical formulation," as used herein, means any formulation which is pharmaceutically acceptable for administration of a compound as described herein by e.g., injection, oral administration, topical application etc. In certain embodiments as described herein, the topical formulation comprises an excipient system. Pharmaceutically effective excipients include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other excipient known in the art for topically administering pharmaceuticals. A more complete listing of art-known carvers is provided by reference texts that are standard in the art, for example, *Remington's Pharmaceutical Sciences,* 16th Edition, 1980 and 17th Edition, 1985, both published by Mack Publishing Company, Easton, Pa., the disclosures of which are incorporated herein by reference in their entireties. In certain other embodiments the formulations useful with the methods and assays described herein can further comprise excipients. Any pharmaceutically acceptable excipient known in the art can be used to prepare the inventive pharmaceutically acceptable formulations. Examples of excipients that can be included in the formulations described herein include, but are not limited to, preservatives, antioxidants, moisturizers, emollients, buffering agents, solubilizing agents, other penetration agents, skin protectants, surfactants, and propellants, and/or additional therapeutic agents used in combination with the compound(s) described herein. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyarrisole, tocopherols, and chelating agents like EDTA and citric acid. Suitable moisturizers include, but are not limited to, glycerine, sorbitol, polyethylene glycols, urea, and propylene glycol. Suitable buffering agents for use with the compositions described herein include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the compounds described herein include, but are not limited to, vitamin E oil, allatoin, dimethicone, glycerin, petrolatum, and zinc oxide.

In one embodiment, the compositions described herein are formulated for topical administration. In some embodiments, the pharmaceutically acceptable topical formulations as contemplated herein comprise at least a compound as described herein and a penetration enhancing agent. The choice of topical formulation will depend or several factors, including the condition to be treated, the physicochemical characteristics of the administered compound and other excipients present, their stability in the formulation, available manufacturing equipment, and costs constraints. As used herein the term "penetration enhancing agent" means an agent capable of transporting a pharmacologically active compound through the stratum coreum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the compositions described herein include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

In certain embodiments, the compositions can be in the form of ointments, pastes, creams, lotions, gels, powders, solutions, sprays, inhalants or patches. In certain exemplary embodiments, formulations of the compositions can further contain saturated or unsaturated fatty acids such as stearic acid, palmitic acid, oleic acid, palmito-oleic acid, cetyl or oleyl alcohols, stearic acid being particularly preferred. Such compositions can also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulation, eardrops, and eye drops are also contemplated herein. Additionally, the assays and methods described herein contemplate the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

It will also be appreciated that the compounds and pharmaceutical compositions described herein can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent or anti-cancer agent), or they may achieve different effects (e.g., control of any adverse effects).

For example, other therapies or anticancer agents that can be used in combination with the compounds as described herein for cancer therapy include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferon, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ion (Cisplatin, Carboplatin), enzymes (Asparaginase), and hormones (Tamoxifen, Leuprelide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/draglis&ame).

In certain embodiments, the pharmaceutical compositions described herein further comprise one or more additional therapeutically active ingredients (e.g., chemotherapeutic and/or palliative). The term "palliative" refers to treatment that is focused on the relief of symptoms of a disease and/or side effects of a therapeutic regimen, but is not curative. For example, palliative treatment encompasses painkillers, antinausea medication and anti-sickness drugs. In addition, chemotherapy, radiotherapy and surgery can all be used palliatively (that is, to reduce symptoms without going for cure;

e.g., for shrinking tumors and reducing pressure, bleeding, pain and other symptoms of cancer).

Additionally, the compositions for use with the assays and methods described herein can include pharmaceutically acceptable derivatives of the compounds, and methods of treating a subject using these compounds, pharmaceutical compositions thereof, or either of these in combination with one or more additional therapeutic agents.

Another aspect described herein relates to a kit for conveniently and effectively carrying out the methods and assays as described herein. In general, the pharmaceutical pack or kit comprises one or more containers filled with one or more of the ingredients of the pharmaceutical compositions as described herein. Optionally associated with such container(s) can be a notice in the form prescribed by a governmental agency regulating the manufacture, use or sale of pharmaceutical products, which notice reflects approval by the agency of manufacture, use or sale for human administration.

Apoptosis and Disease

Deregulated apoptosis (e.g., increased or decreased apoptosis above that observed in a normal, healthy subject free from detectable disease) has been shown to be involved in the pathogenesis of certain disease states. For example, impaired apoptosis plays a role in the development of tumors, cancers, autoimmune disease, and inflammatory disorders due to the survival of cells that would normally be targeted for apoptotic cell death. Alternatively, excessive apoptosis can result in damage and/or loss of cells necessary for normal physiological responses (e.g., lymphocyte loss occurs in HIV infected individuals), and can lead to degenerative diseases, including e.g., neurodegenerative diseases such as Parkinson's disease, Alzheimer's disease, and dementia, among others. Thus, the detection and/or quantification of apoptosis in a biological sample can provide valuable diagnostic information regarding the presence or level of disease in a subject. In addition, detection and/or quantification of apoptosis in a biological sample can permit one of skill in the art to monitor efficacy of a therapeutic agent (e.g., an anti-cancer agent) known to modulate cell survival via an apoptotic signaling pathway.

Cancer: In one embodiment of the methods, the subject has a tumor or a cancer. As used herein, "cancer" refers to any of various malignant neoplasms characterized by the proliferation of anaplastic cells that can invade surrounding tissue and/or metastasize to new body sites and also refers to the pathological condition characterized by such malignant neoplastic growths.

In one embodiment, the methods and assays described herein further comprise a step of selecting a subject who has been diagnosed with cancer. Methods of diagnosing cancer are known to a skilled physician. In general, cancer is suspected based on a person's symptoms, the results of a physical examination, and the results of screening tests such as imaging. Imaging tests often include plain x-rays, ultrasonography, CT, and MRI. These tests assist in identifying abnormalities, determining qualities of a mass (solid or cystic), providing dimensions, and establishing relationship to surrounding structures, which can be important if surgery or biopsy is being considered. Occasionally, x-rays obtained for other reasons, such as an injury, show abnormalities that might be cancer. Confirmation that cancer is present requires other tests (termed diagnostic tests e.g., by tumor biopsy and histopathologic examination). Other screening tests include but are not limited to screening the level of serum tumor markers the findings of which are suggestive of a specific cancer. Such serum tumor markers include, but are not limited to, α-Fetoprotein (hepatocellular carcinoma, testicular carcinoma), carcinoembryonic antigen (colon cancer), β-human chorionic gonadotropin (choriocarcinoma, testicular carcinoma), serum immunoglobulins (multiple myeloma), DNA probes (e.g., bcr probe to identify a chromosome 22 alteration in chronic myelogenous leukemia), CA 125 (ovarian cancer), CA 27-29 (breast cancer), prostate-specific antigen (prostate cancer).

After cancer is diagnosed, it can be "staged." Staging is a way of categorizing or describing how extensive or advanced the cancer is in terms of its location, size, growth into nearby structures, and spread to other parts of the body. Staging allows doctors to determine the most appropriate treatment as well as helping to determine prognosis. Staging can be performed using scans or other imaging tests, such as x-ray, CT, MRI, bone scintigraphy, or positron emission tomography (PET). The choice of staging test(s) depends on the type of cancer, as different cancers involve different parts of the body. As but one example, CT scanning is used to detect cancer in many parts of the body, including the brain and lungs and parts of the abdomen, including the adrenal glands, lymph nodes, liver, and spleen. Alternatively, MRI is of particular value in detecting cancers of the brain, bone, and spinal cord.

Biopsies are often needed for staging and can sometimes be done together with the initial surgical treatment of a cancer. For example, during surgery for breast cancer, the surgeon can biopsy or remove lymph nodes located in the armpit to determine whether the breast cancer has spread there; this information along with features of the primary tumor helps the doctor determine whether further treatment is needed. When staging is based only on initial biopsy results, physical examination, and imaging, the stage is referred to as clinical. When the doctor uses results of a surgical procedure or additional biopsies, the stage is referred to as pathologic. The clinical and pathologic stage may differ. In addition to imaging tests, doctors can obtain a blood test(s) to see if the cancer has begun to affect the liver, bone, or kidneys.

Examples of cancer include but are not limited to, carcinoma, lymphoma, blastoma, sarcoma, and leukemia. Some exemplary cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia;

chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the carcinoma or sarcoma includes, but is not limited to, carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include but are not limited to papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include but are not limited to, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

In one embodiment of the methods, the subject having the tumor, cancer or malignant condition is undergoing, or has undergone, treatment with a cancer therapy. In some embodiments, the cancer therapy is chemotherapy, radiation therapy, immunotherapy or a combination thereof.

Biological Samples and Detecting Apoptosis Therein

A biological sample can be obtained from essentially any tissue comprising or suspected of comprising an apoptotic cell(s). Some non-limiting examples of tissues include e.g., brain, liver, lung, gut, stomach, fat, muscle, spleen, testes, uterus, urinary tract, bladder, prostate, esophagus, ovary, skin, endocrine organ and bone, etc. In one embodiment, a biological sample comprises cells including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. In one embodiment, the biological sample is a biopsy from a growth or tumor.

In one embodiment, the biological sample comprises a tissue biopsy, such as, an aspiration biopsy, a brush biopsy, a surface biopsy, a needle biopsy, a punch biopsy, an excision biopsy, an open biopsy, an incision biopsy or an endoscopic biopsy, or a tumor sample. Biological samples can also be biological fluid samples, including but not limited to, urine, blood, serum, platelets, saliva, cerebrospinal fluid, nipple aspirates, circulating tumor cells, and cell lysate (e.g. supernatant of whole cell lysate, microsomal fraction, membrane fraction, exosomes, or cytoplasmic fraction). Samples can be obtained by any method known to one of skill in the art including e.g., needle biopsy, fine needle aspiration, core needle biopsy, vacuum assisted biopsy, open surgical biopsy, among others.

In one embodiment, the level of apoptosis is detected in vitro. That is, a biological sample of the tissue is extracted from in the subject. In one embodiment, the biopsy tissue sample is sent to a laboratory for analysis. In one embodiment, the biopsy tissue sample is analyzed at the site where the biopsy extraction occurred, e.g., the doctor's office or surgical procedure room. The use of a commercial apoptosis kit will be convenient for this purpose. As such, in one embodiment, the biological sample is contacted with a compound as described herein.

In one embodiment, the biological sample is fixed or cryopreserved before analysis, i.e., contacting with a compound as described herein. In one embodiment, the biological sample is fixed or cryopreserved immediately upon extraction from the subject. In one embodiment, the biological sample is fixed or cryopreserved within one hour of extraction. In one embodiment, the biological sample is fixed or cryopreserved no more than five hours following extraction from the subject. Methods of fixing tissue samples are well known in the art, e.g., with paraformaldehyde.

In one embodiment, the biological sample is analyzed as soon as it was extracted from the subject. In one embodiment, the biological sample is analyzed within one hour of extraction. In one embodiment, the biological sample is analyzed no more than five hours after extraction.

In one embodiment, detection and/or quantification of apoptosis is performed in vivo. The tissue in the subject that is to be analyzed is contacted with a compound as described herein in vivo. In one embodiment, contacting is by way of administering one or more compounds as described herein to the subject. In one embodiment, if the tissue is accessible by direct injection, e.g., breast and skin cancer, the compound can be injected directly into the tissue. In one embodiment, if the tissue is not easily accessible by direct injection, a catheter can used to deliver the compound to the tissue, e.g., by intravenous injection, preferably to the blood vessel/artery as close to the tissue as possible or to a blood vessel/artery supplying the tissue, e.g., hepatic artery for liver cancer or carotid artery for brain tumor. Exemplary modes of administration for use in the methods described herein include, but are not limited to, injection, intrapulmonary (including intranasal and intratracheal) infusion, and inhalation as an aerosol (including intranasal). "Injection" includes, without limitation, intravenous, intramuscular, intraarterial, intradermal, intraperitoneal, transtracheal and subcutaneous. The phrases "parenteral administration" and "administered parenterally" as used herein, refer to modes of administration other than enteral and topical administration, usually by injection, and includes, without limitation, intravenous, intraperitoneal, intramuscular, intraarterial, intradermal, transtracheal, and subcutaneous administration.

In one embodiment, the level of apoptosis is detected in vivo by detecting fluorescence from a compound as described herein. Alternatively, the level or apoptosis is detected in vivo by detecting a signal from a detectable label of a compound as described herein. Depending on the type of label, a skilled clinician can select an appropriate detectable method for the specific detectable signal emitted by the labeled compound or the fluorescent compound itself. In one embodiment, the fluorescence or detectable signal from the compound as described herein is detected by an MRI scan, a CT scan, an NIR scan or a PET scan. In one embodiment of the methods, the compound comprises a label such as a fluorescent label, a colorometric dye, a magnetic resonance imaging contrast label, a radioisotope, a biotin or a positron emission tomography imaging label.

In one embodiment, the detection of apoptosis can be in vitro, in situ, ex vivo or in vivo.

Reference Sample

The terms "reference level," "reference sample," and "reference" are used interchangeably herein and refer to the level of apoptosis in a known sample against which another sample is compared (i.e., obtained from a subject having a cancer and/or being treated for such cancer). A standard is useful for determining the presence of apoptosis, quantifying the level of apoptosis, or determining the relative increase/decrease of apoptosis in a biological sample. A standard serves as a reference level for comparison, such that samples can be normalized to an appropriate standard in order to infer the presence, absence or extent of apoptosis in a subject.

In one embodiment, a biological standard is obtained at an earlier time point (for example, prior to the onset of treatment with an apoptotic modulator) from the same individual that is to be tested or treated as described herein. Alternatively, a standard can be from the same individual having been taken at a time after the onset or diagnosis of a treatment with a therapeutic agent that modulates apoptosis. In such instances, the standard can provide a measure of the efficacy of treatment.

A standard level can be obtained, for example, from a known biological sample from a different individual (e.g., not the individual being tested) that is substantially free of apoptosis (e.g., a healthy individual or a subject having cancer but not undergoing treatment). A known sample can also be obtained by pooling samples from a plurality of individuals to produce a standard over an averaged population, wherein a standard represents an average level of apoptosis among a population of individuals (e.g., a population of individuals having a certain cancer or a population of individuals being treated for the cancer). Thus, the level of apoptosis in a standard obtained in this manner is representative of an average level of apoptosis in a general population of individuals having cancer, or a population of individuals being treated for such a cancer. An individual sample is compared to this population standard by comparing the level or degree of apoptosis from a sample relative to the population standard. Generally, an increase in the amount of apoptosis over the standard (e.g., a reference obtained from subjects having a cancer) will indicate that apoptosis is increased, and in the setting of cancer, that the treatment is an effective pro-apoptotic treatment. Conversely, a decrease in the amount of apoptosis in such subjects will indicate that the cancer is not responding well to the therapeutic agent. The converse is contemplated in cases where a standard is obtained from a population of subjects having over-active apoptotic pathways, such as those suffering from a neurodegenerative disorder. That is, an increase in apoptosis detection or quantity can indicate the presence or progression of disease, while a decrease in apoptosis detection or quantity can indicate that the treatment is efficacious. It should be noted that there is often variability among individuals in a population, such that some individuals will have higher levels of apoptosis, while other individuals have lower levels of apoptosis. However, one skilled in the art can make logical inferences on an individual basis regarding the detection and treatment of cancer (or other disorder related to deregulated apoptosis) as described herein.

A standard or series of standards can also be synthesized. A known amount of apoptotic cells (or a series of known amounts) can be prepared within the typical range of apoptosis that is observed in a general cancer population. This method has an advantage of being able to compare the extent of disease in one or more individuals in a mixed population. This method can also be useful for subjects who lack a prior sample to act as a standard or for routine follow-up post-diagnosis. This type of method can also allow standardized tests to be performed among several clinics, institutions, or countries etc.

In one embodiment, a negative control reference is the average amount of fluorescence measured in healthy biological samples or tissues that are not known to be undergoing apoptosis. The biological samples or tissues can be those obtained for a control population of healthy patients.

Selecting a Subject

Accordingly, in one embodiment, provided herein are rapid assays or methods for selecting an effective treatment for a subject in need thereof, the method comprising detecting a level of apoptosis in a tissue in a subject after the start of treatment and comparing the detected level of apoptosis to a control reference or background reference wherein if the detected level of apoptosis is above a control reference or background indicates that the treatment is effective and the treatment should be continued, and wherein if the detected level of apoptosis is below or no different than the control reference or background indicates that the treatment is not effective and the treatment should be discontinued.

In one embodiment, the subject is diagnosed with a medical ailment or disease wherein cell death or apoptosis is one desired effect of the treatment of the medical ailment or disease, e.g., cancer.

In one embodiment of the method, the method further comprises a step of selecting a subject who is diagnosed with a medical ailment or disease wherein cell death or apoptosis is one desired effect of the treatment of the medical ailment or disease.

In another embodiment, the subject is diagnosed with a medical ailment or disease wherein cell death or apoptosis is a consequential effect of the ailment or disease, e.g., an autoimmune disease, organ transplant rejection etc.

Accordingly, in this embodiment, provided herein is a rapid method of selecting an effective treatment for a subject in need thereof, the method comprising detecting a level of apoptosis in a tissue in a subject after the start of treatment and comparing the detected level of apoptosis to a control reference or background reference wherein if the detected level of apoptosis is above a control reference or background indicates that the treatment is ineffective and the treatment should not be continued, and wherein if the detected level of apoptosis is below or no different than the control reference or background indicates that the treatment is effective and the treatment should be continued, wherein the treatment is for a medical ailment or disease wherein cell death or apoptosis is a consequential effect of the ailment or disease. In one embodiment of this method, the method further comprises selecting a subject who is diagnosed with a medical ailment or disease wherein cell death or apoptosis is a consequential effect of the ailment or disease.

In one embodiment, the level of apoptosis in a tissue in the subject is analyzed shortly after the start of treatment. In one embodiment, the level of apoptosis in a tissue in the subject is analyzed within the period of less than a week and anytime up to two weeks after the start of treatment. In some embodiments, the analysis is performed on the first, second, third, fourth, five, sixth, seventh, eighth, ninth, tenth, eleventh, twelfth, thirteenth or fourteenth day after the start of treatment.

Treatment of Cancer

In some embodiments, a subject being treated with an anti-cancer therapy is evaluated by detecting the level of apoptosis in a biological sample obtained from the subject. In some embodiments, the subject being treated for cancer is administered one or more anti-cancer or chemotherapeutic agents.

Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analoguess such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; chloranbucil; GEMZAR® gemcitabine; 6-thioguanine; mercaptopurine; platinum analogs such as cisplatin, oxaliplatin and carboplatin; vinblastine; platinum; etoposide (VP-16); ifosfamide; mitoxantrone; vincristine; NAVELBINE®. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

Dosage and Administration

In one aspect, the methods described herein provide assays and methods for detecting apoptosis in a biological sample obtained from a subject, and optionally treating the subject with a therapeutic agent. In one embodiment, the subject can be a mammal. In another embodiment, the mammal can be a human, although the approach is effective with respect to all mammals. In one embodiment, the method comprises administering to the subject an effective amount of a pharmaceutical composition comprising a therapeutic agent, in a pharmaceutically acceptable carrier. In another embodiment, the methods or assays comprise administering to the subject an effective amount of a pharmaceutical composition comprising a compound as described herein for in vivo or in situ detection of apoptosis in the subject.

The dosage range for the therapeutic agent or compound as described herein depends upon the potency, and includes amounts large enough to produce the desired effect, e.g., detection of apoptosis or treatment of a cancer. The dosage should not be so large as to cause unacceptable adverse side effects. Generally, the dosage will vary with the type of agent or composition (e.g., an antibody or fragment, fluorescent compound, small molecule, siRNA, etc.), and with the age, condition, and sex of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 μg/kg body weight. Alternatively, the dose range will be titrated to maintain serum levels between 5 μg/mL and 30 μg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in e.g., degree or level of apoptosis, number of apoptotic cells, tumor size, tumor volume, tumor growth rate, etc. (see "Efficacy Measurement" below). Such effective amounts can be gauged in clinical trials as well as animal studies for a given inhibitor.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. For the treatment of tumors, the agent can be administered systemically, or alternatively, can be administered directly to the tumor e.g., by intratumor injection or by injection into the tumor's primary blood supply.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent or compound as described herein can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent or compound as described herein permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

In some embodiments of the methods described herein, a subject is treated with a combination of therapeutic agents. In such a combination therapy, an agent (e.g., an anti-cancer) can be administered before, during, or after commencing therapy with another agent, as well as any combination thereof, i.e., before and during, before and after, during and after, or before, during and after commencing the combination therapy. Also, in general, the therapeutic agents do not have to be administered in the same pharmaceutical composition, and can, because of different physical and chemical characteristics, be administered by different routes. For example, an agent can be administered orally to generate and maintain appropriate therapeutic blood levels thereof, while another agent can be administered by inhalation, or vice versa. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Monitoring Efficacy of a Therapy

In one embodiment, provided herein is a method for measuring the efficacy of a treatment (e.g., an anti-cancer therapy) in a patient in need thereof, the method comprising (i) detecting a level of apoptosis in the subject using any of the methods described herein prior to administering a treatment and (ii) detecting a level of apoptosis in the subject using any of the methods described herein after administering the treatment, wherein a difference in the level of apoptosis in the subject after administering the treatment relative to the level of apoptosis in the subject before administering the treatment is indicative of the treatment being effective.

It is also contemplated that during the course of treatment, the level of apoptosis in the subject is monitored over a period of time. In the embodiments where multiple measurements of the level of apoptosis in the subject are taken, it is contemplated, but not required, that the level of apoptosis in the subject at a later time period during the course of treatment is compared to the level of apoptosis in the same subject an earlier time period during the course of treatment.

In one embodiment, provided herein is a method for measuring the efficacy of a treatment in a patient in need thereof, the method comprising (i) detecting a level of apoptosis in the subject using any of the methods described herein at a first time period after administering a treatment and (ii) detecting a level of apoptosis in the subject using any of the methods described herein at a first time period after administering the treatment, wherein the first time period is later than the second time period, (iii) comparing the levels of (i) with (ii) wherein a difference in the level of apoptosis in the subject the second time period relative to the level of apoptosis to the first time period is indicative of the treatment being effective.

In one embodiment, one of the treatment's goals is to arrest or reduce apoptosis, e.g., immune suppression for organ transplant rejection. In another embodiment, one of the treatment's goals is to promote or increase apoptosis, e.g., an anti-cancer treatment.

In some embodiments of the aspect, the level of apoptosis is increased, e.g., following a cancer treatment. In other embodiments, the level of apoptosis is decreased, e.g., in organ transplant rejection, occlusion vascular disease, or infection. In some embodiments, the increase is at least 5% compared to the level of apoptosis in a reference sample. In other embodiments, the increase is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least 100%, at least 2-fold, at least 5-fold, at least 10-fold, at least 100-fold or higher above the level of apoptosis prior to treatment or as compared to a reference value or range of values. In some embodiments, the decreased level of apoptosis in a biological sample is at least 5% lower than the level of apoptosis in a reference sample. In other embodiments, the decrease is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or even 100% (e.g., absent or below detectable limits using the assays or compounds described herein) below the level of apoptosis of the reference sample or in a sample obtained prior to initiation of a treatment.

In some embodiments, the methods described herein provide rapid results to determine whether a treatment is working or not at an early phase of the treatment. The method also provides a rapid method of selecting an effective treatment for a subject in need thereof, where there are several treatment options for the subject or the particular ailment or disease. For example, in a typical breast cancer treatment, the subject may be treated with e.g., chemotherapy (CMF: cyclophosphamide, methotrexate, and fluorouracil) and/or irradiation therapy, for a period of one or two months after which the treatment efficacy is assessed. Methods of assessing cancer treatment efficacy are well known in the art to a skilled clinician, physician or oncologist. Rather than waiting for one or two months for the chemotherapy or radiation to shrink the tumors and/or reduce the level of circulating cancer biomarkers, the methods described herein can be used within the first few doses of chemotherapy or radiation, within the period of less than a week and anytime up to two weeks after the start of treatment. The methods allow the clinician to quickly determine if the specific chemotherapy or radiation is effective in inducing apoptosis of the cancer cells by way of detecting an increase in the level of apoptosis using the compositions and assays described herein. If the first few cancer treatment doses resulted in no detectable increase in apoptosis at the tumor site(s), this indicates that the specific treatment protocol is not working. The clinician can then change to another treatment protocol, for example, by altering the dose of the agent, the frequency of delivery or switching to a different therapy altogether. For example, one of skill in the art can opt to change a CMF (cyclophosphamide, methotrexate and fluorouracil 5FU) chemotherapy to a GET (gemcitabine, epirubicin, and taxol) therapy. Early evaluation of treatment efficacy allows the clinician to try several treatments options and select an effective one within a relatively short period of time after the initial diagnosis and/or staging of cancer, before the cancer has spread extensively and progress to a late stage cancer. Early identification of an effective treatment protocol reduces the time and opportunities for the cancer spread extensively and progress to a late stage cancer and this provides better treatment prognosis for the subject.

The term "effective" when used with respect to a medical ailment or disease treatment protocol refers to a treatment protocol that produces an increase or decrease in the level of apoptosis measured in a biological sample by at least 5% as compared to a reference sample (e.g., the level of apoptosis in a biological sample obtained from the same subject at an earlier time point). The level of apoptosis can be detected and analyzed by any methods known in the art, includes the methods described herein.

Pharmaceutically Acceptable Carriers

The methods of administering a compound as described herein or a therapeutic agent to a subject as described herein involve the use of therapeutic compositions comprising such compounds or therapeutic agents. Therapeutic compositions contain a physiologically tolerable carrier together with the compound or therapeutic agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

A compound or therapeutic agent can also be emulsified or presented as a liposome composition, provided that the emulsification procedure does not adversely affect the activity of the compound or therapeutic agent. The compound and any other active ingredient can be mixed with excipients which are pharmaceutically acceptable and compatible with the active ingredient and in amounts suitable for use in the therapeutic methods described herein.

Additional agents included in a composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the compositions as described herein that is effective in the treatment of a particular disorder or condition will depend on the nature of the disorder or condition, and can be determined by standard clinical techniques.

Systems

Embodiments of the invention also provide for systems (and computer readable media for causing computer systems) to perform a method for detecting apoptosis in a subject, or assessing efficacy of a therapeutic agent that modulates apoptotic pathways.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media #30 can be any available tangible media that can be accessed by a computer. Computer readable storage media includes volatile and non-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can be accessed by a computer including and any suitable combination of the foregoing.

Computer-readable data embodied on one or more computer-readable storage media can define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium as described herein, may be distributed across one or more of such components.

The computer-readable storage media can be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, a storage device #30, a comparison module #80, and a display module #110. The functional modules can be executed on one, or multiple, computers, or by using one, or multiple, computer networks. The determination system has computer executable instructions to provide e.g., expression information in computer readable form.

The determination system #40, can comprise any system for detecting a signal representing the level of apoptosis in a sample. Such systems can include microscope data acquisition system, fluorescence data, etc.

The information determined in the determination system can be read by the storage device #30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon values representing information relating to the detection and/or quantification of the level of apoptosis. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising expression information.

In one embodiment the reference data stored in the storage device to be read by the comparison module is e.g., apoptosis data obtained from a population of subjects that are being treated with a particular anti-cancer agent.

The "comparison module" #80 can use a variety of available software programs and formats for the comparison operative to compare sequence information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the detection and/or level of apoptosis in a subject.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application can include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in one embodiment of the systems described herein, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide content based in part on the comparison result that may be stored and output as requested by a user using a display module #110.

The content based on the comparison result, can be e.g., the level of apoptosis (e.g., number or percentage of apoptotic cells) compared to a reference indicating the presence of apoptosis and/or therapeutic efficacy in a subject. Alternatively, the content based on the comparison result can be e.g., the absence of apoptosis compared to a reference indicating the absence of apoptosis or a non-efficacious therapeutic regimen in an individual.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for detecting apoptosis in a subject.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Kits

A kit is any manufacture (e.g., a package or container) comprising at least one reagent, e.g., a fluorescent compound of Formula (I), (IIa), (IIIa) or (IIIb) as described herein, the manufacture being promoted, distributed, or sold as a unit for performing the methods or assays described herein. When the kits, and methods described herein are used for diagnosis and/or monitoring treatment of e.g., cancer, the compounds, detection probes or systems can be selected such that a positive result is obtained in at least about 20%, at least about 40%, at least about 60%, at least about 80%, at least about 90%, at least about 95%, at least about 99% or in 100% of subjects afflicted with a cancer and/or being treated with an anti-cancer agent.

When the level of apoptosis is used in the methods and assays described herein, the level of apoptosis (e.g., number of apoptotic cells) can be compared with the level of apoptosis in non-cancerous samples of the same type or to another reference standard as described herein.

The kits described herein include methods for assaying for apoptotic cells in a sample (e.g., an archived tissue sample or a sample obtained from a subject). The kits described herein comprise components useful for assessing the presence of apoptotic cells (e.g., in a sample such as a subject sample). The kit can comprise one or more reagents capable of detecting apoptotic cells e.g., one or more compounds of Formula (I), (II), (IIIa), or (IIIb). Such components or reagents can permit detection of apoptotic cells or apoptotic levels directly using e.g., a fluorescent compound, detectable labels or indirectly e.g., detection of DNA laddering.

The kits described herein can optionally comprise additional components useful for performing the methods and assays described herein. By way of example, the kit can comprise fluids (e.g., SSC buffer) suitable for use of the compounds as described herein, one or more sample compartments, an instructional material which describes performance of a method as described herein, a sample of normal cells, a sample of apoptotic cells, and the like.

This invention is further illustrated by the following example which should not be construed as limiting. The contents of all references cited throughout this application, as well as any figures and tables are hereby incorporated by reference in their entirety.

Those skilled in the art will recognize, or be able to ascertain using not more than routine experimentation, many equivalents to the specific embodiments of the invention described herein. Such equivalents are intended to be encompassed by the following claims.

EXAMPLES

Provided herein are data relating to a systematic investigation on the altered membrane permeability of apoptotic cells.

The results shown herein indicate that simple modification to the chemical structure of commonly used fluorophores converts them into compounds useful as specific markers for apoptosis. The plasma membrane of apoptotic cells appears to be permeable to molecules of various functional groups and charge, but does discriminate against molecules of large size. The new findings reported herein facilitate the development of noninvasive imaging agents for apoptosis.

Noninvasive imaging of apoptosis is highly desirable for the diagnosis of a variety of diseases, as well as for the early prognosis of anticancer treatments (J. F. Tait, *J. Nucl. Med.,* 2008, 49, 1573-1576; A. Reshef et al., *J Nucl Med,* 2010, 51, 837-840; D. Park et al., *J. Am. Chem. Soc.,* 2011, 133, 2832-2835). There are a number of strategies that effectively detect apoptosis in vitro (S. H. Kaufmann et al., *Methods,* 2008, 44, 262-272; M. van Engeland et al., *Cytometry,* 1998, 31, 1-9; O. Kepp et al., *Nat Rev Drug Discov,* 2011, 10, 221-237). However, it has been challenging to adapt them to noninvasive imaging of apoptotic cell death in the clinic. For example, Annexin V is well known to selectively bind apoptotic cells by targeting the surface-exposed phosphatidylserine (PS) (M. A. Swairjo et al., *Nat. Struct. Biol.,* 1995, 2, 968-974). Despite its wide application in cell biology research (M. van Engeland et al., *Cytometry,* 1998, 31, 1-9), radiolabeled annexin V was shown to be problematic for in vivo imaging for several reasons including poor tissue penetration and slow clearance (L. L. Johnson et al., *J. Nucl. Med.,* 2005, 46, 1186-1193; M. Kartachova et al., *J. Clin. Oncol.* 2007, 25, 2534-2539). It has been suggested that these general problems affiliated with large proteins can be circumvented by low-molecular weight agents that selectively label apoptotic cells (A. Reshef et al., *J Nucl Med,* 2010, 51, 837-840).

In an effort to develop small molecule markers for apoptosis, the present study targeted several characteristic features of apoptosis including caspase activity (L. E. Edgington et al., *Nat. Med.,* 2009, 15, 967-973) and surface-exposed PS (R. G. Hanshaw and B. D. Smith, *Bioorg Med Chem,* 2005, 13, 5035-5042; R. G. Hanshaw et al., *ChemBioChem,* 2005, 6, 2214-2220; H. Zheng et al., *Journal of the American Chemical Society,* 2011, 133, 15280-15283; C. Burtea et al., *Mol. Pharm.,* 2009, 6, 1903-1919; N. Thapa et al., *J Cell Mol Med,* 2008, 12, 1649-1660). Besides these well-known characteristics, several reports indicate that apoptotic cells differ in membrane permeability from healthy cells as well (T. Idziorek et al., *J. Immunol. Methods,* 1995, 185, 249-258; M. Damianovich et al., *Eur J Nucl Med Mol Imaging,* 2006, 33, 281-291; R. Aloya et al., *Apoptosis,* 2006, 11, 2089-2101; A. Cohen et al., *Cell Res,* 2009, 19, 625-637). However, the origin of the altered membrane permeability is poorly understood (F. B. Chekeni et al., *Nature,* 2010, 467, 863-867), as is the scope of molecular structures that can permeate through apoptotic cell membranes.

Herein the inventors document a systematic investigation of the membrane permeability of apoptotic cells. The results of the study indicate that simple modification of commonly used dyes (e.g. fluorescein) permits specific entry into cells at the early stages of apoptosis, thus expanding the pool of small molecules for imaging cell death. Dyes of the fluorescein family are among the most widely used fluorescence reporters in chemical and biomedical research. The parent compound fluorescein does not differentiate between healthy and apoptotic cells. Indeed, when fluorescein is subjected to flow cytometry analysis of Jurkat cells (FIG. 1A), the same degree of staining was observed for the cells treated with and without camptothecin (CPT), a topoisomerase inhibitor known to induce apoptosis of Jurkat cells (R. G. Hanshaw et al., *ChemBioChem,* 2005, 6, 2214-2220).

Figure 1B:
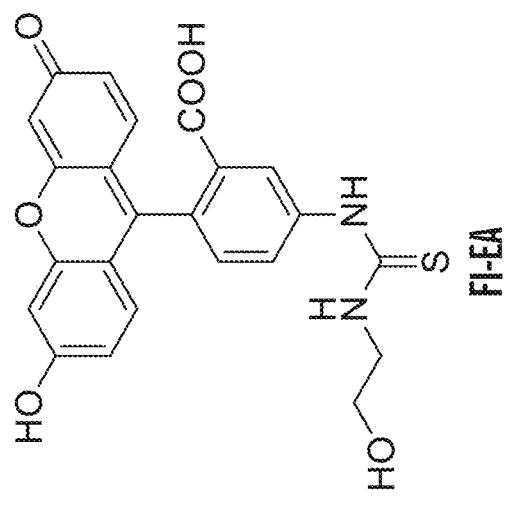
Figure 1B:
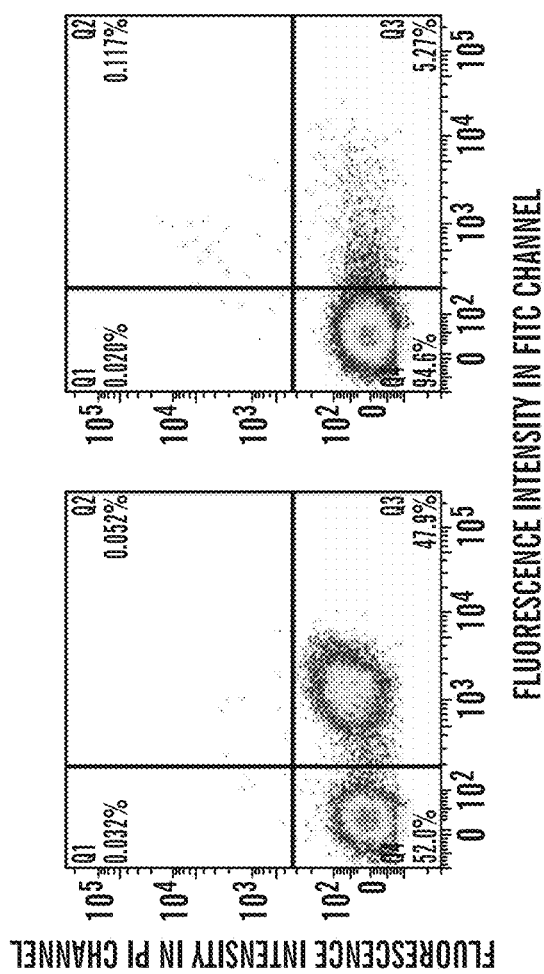
Figure 1C:
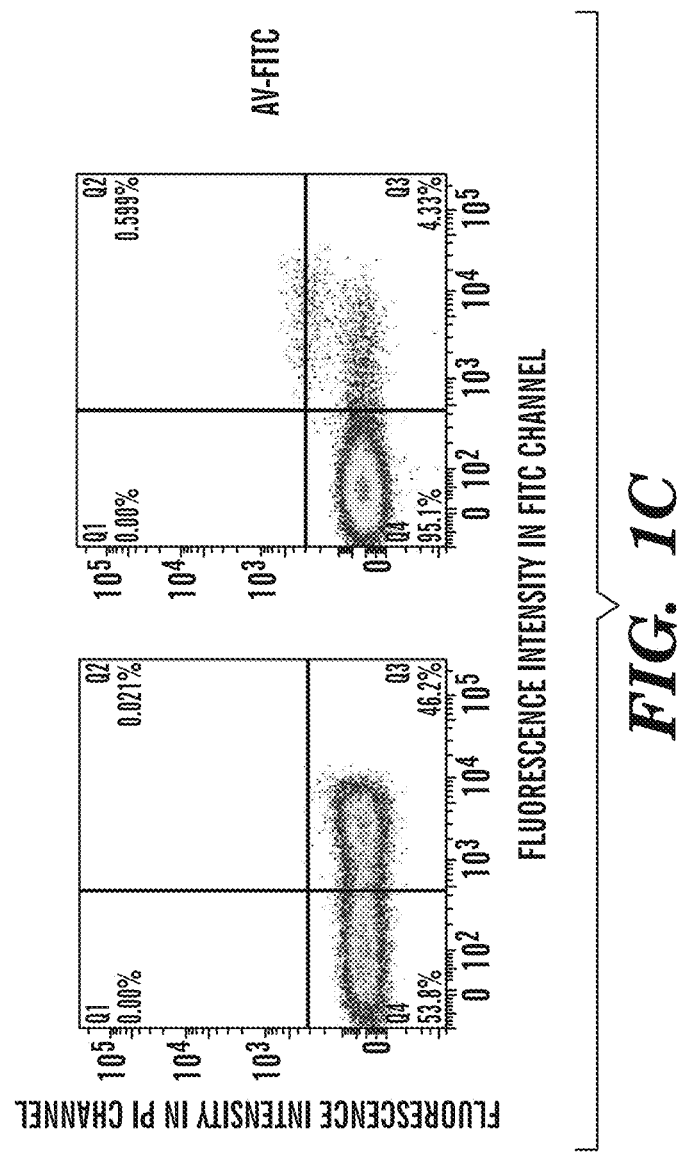

In sharp contrast to fluorescein, the simple derivative F1-EA (FIG. 1B) readily differentiated the cell sample with CPT treatment from the one without. Specifically, F1-EA did not stain untreated cells, but identified two populations for the CPT-treated sample. The population displaying higher fluorescence intensity (the apoptotic cells) constituted ~48% of the total cell population. This agrees with the positive control, in which a FITC (fluorescein isothiocyanate) labeled annexin V (AV-FITC) was used as an apoptosis reporter (FIG. 1C). Also similar to AV-FITC, the F1-EA stained cells showed no fluorescence emission of propidium iodide (PI, the y-axis), a membrane impermeable DNA intercalator. This observation indicates that F1-EA does not stain necrotic or late-stage apoptotic cells.

Figure 2A:
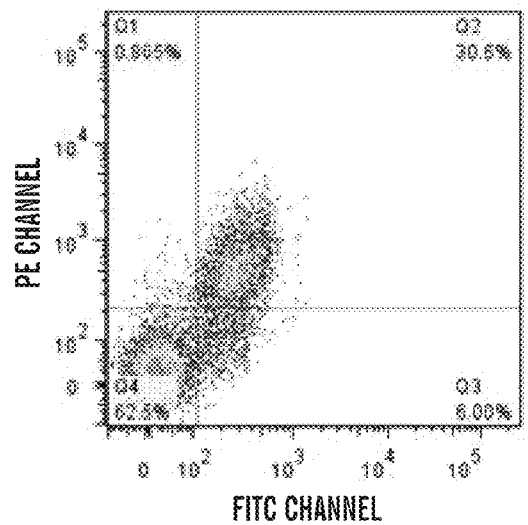
FIGS. 2A-2D depict costaining of apoptotic cells with F1-EZ and AV-PE.
Figure 2B:
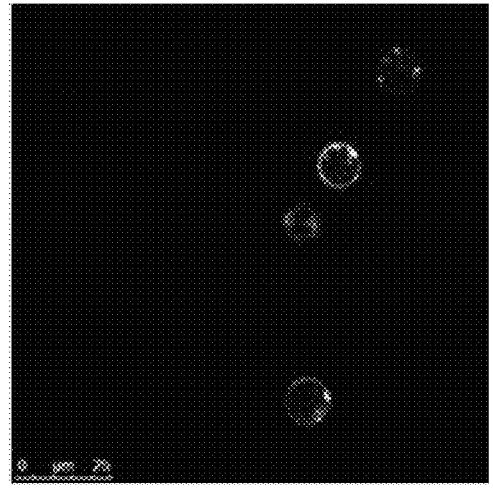
Figure 2D:
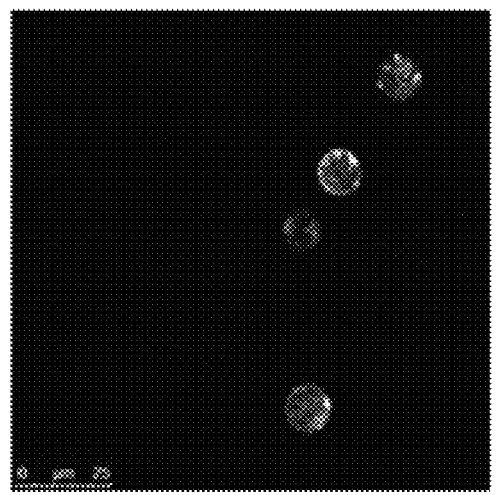
Figure 2C:
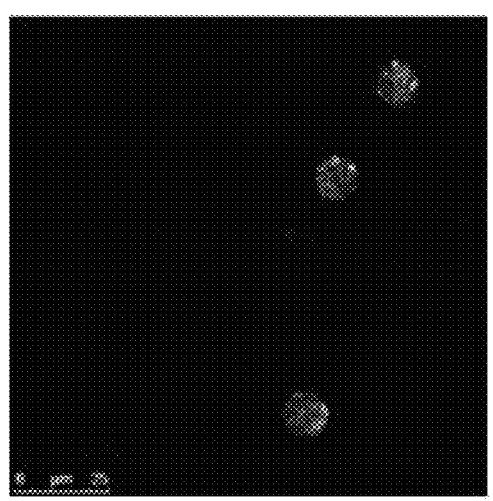

The specificity of F1-EA for apoptotic cells were further validated through a costaining experiment with the R-phycoerythrin labeled annexin V (AV-PE, yellow emission). In presence of both F1-EA and AV-PE, essentially all stained cells converged in the upper right quadrant (FIG. 2A) indicating that each of these cells was stained with AV-PE and F1-EA simultaneously. The flow cytometry result was further validated with confocal microscopy analysis. As expected, the microscopic image revealed the membrane location of AV-PE on the CPT-treated cells (FIG. 2B). In contrast, F1-EA was clearly internalized and evenly distributed in the cytoplasm (FIGS. 2C and 2D). Without CPT treatment, the cells display an interior even darker than the extracellular background, indicating that F1-EA is incapable of permeating through the membrane of healthy cells (FIGS. 5A-5D). Collectively these results support the hypothesis that early apoptotic cells display altered membrane permeability to allow entry of the fluorescein derivative F1-EA.

Using flow cytometry analysis (FIG. 1), healthy cells incubated with fluorescein displayed a higher fluorescence readout than those treated with F1-EA, providing insight into potential mechanisms of nonspecific staining Consistent with the flow cytometry results, confocal imaging of the fluorescein-treated cells showed brighter fluorescence inside the cells in comparison to F1-EA staining (FIGS. 6A-6D). These observations indicate that fluorescein permeates through both healthy and apoptotic cell membranes. The simple modification of fluorescein prohibits entry into healthy cells, and therefore affords the specific staining of apoptotic cells by F1-EA.

Figure 3A:
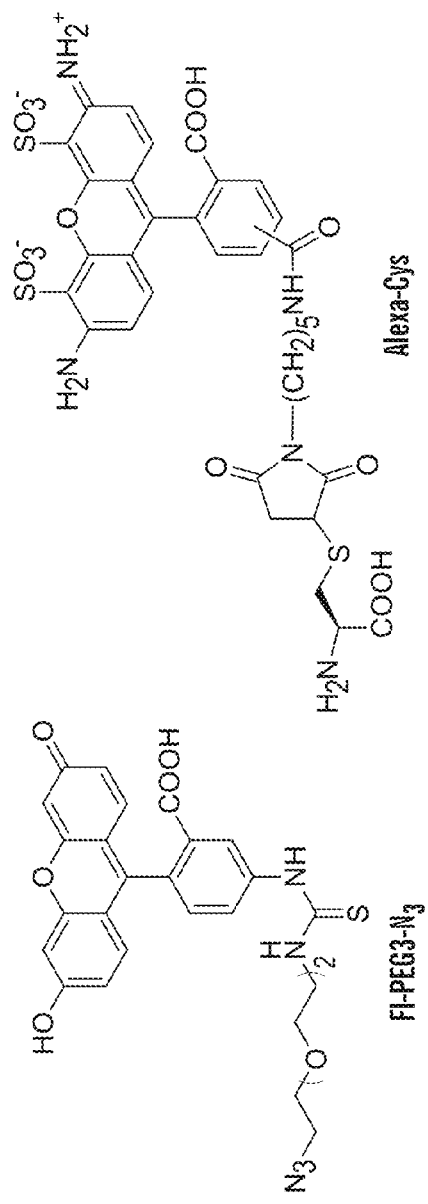
FIGS. 3A and 3B depict the scope of dye derivatives that selectively label apoptotic cells.
Figure 3A:
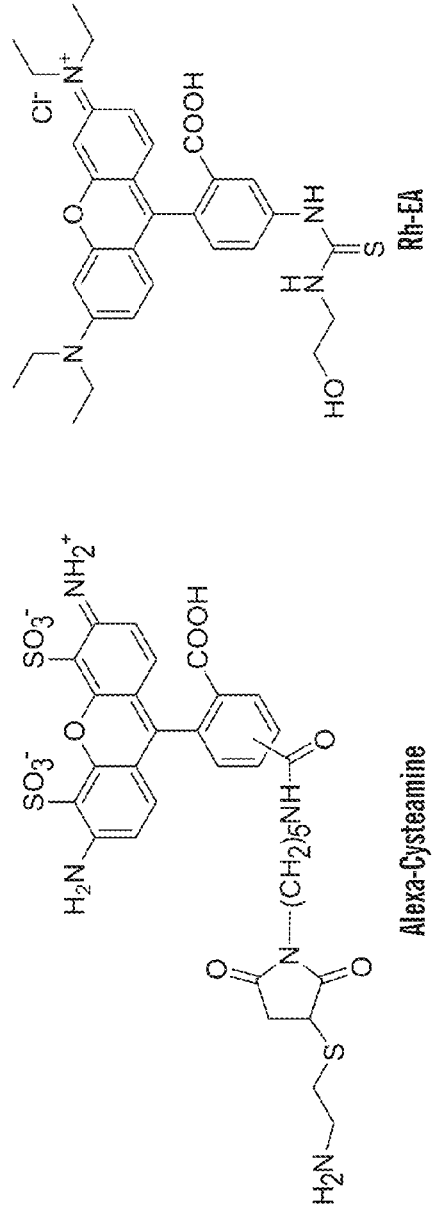
Figure 7:
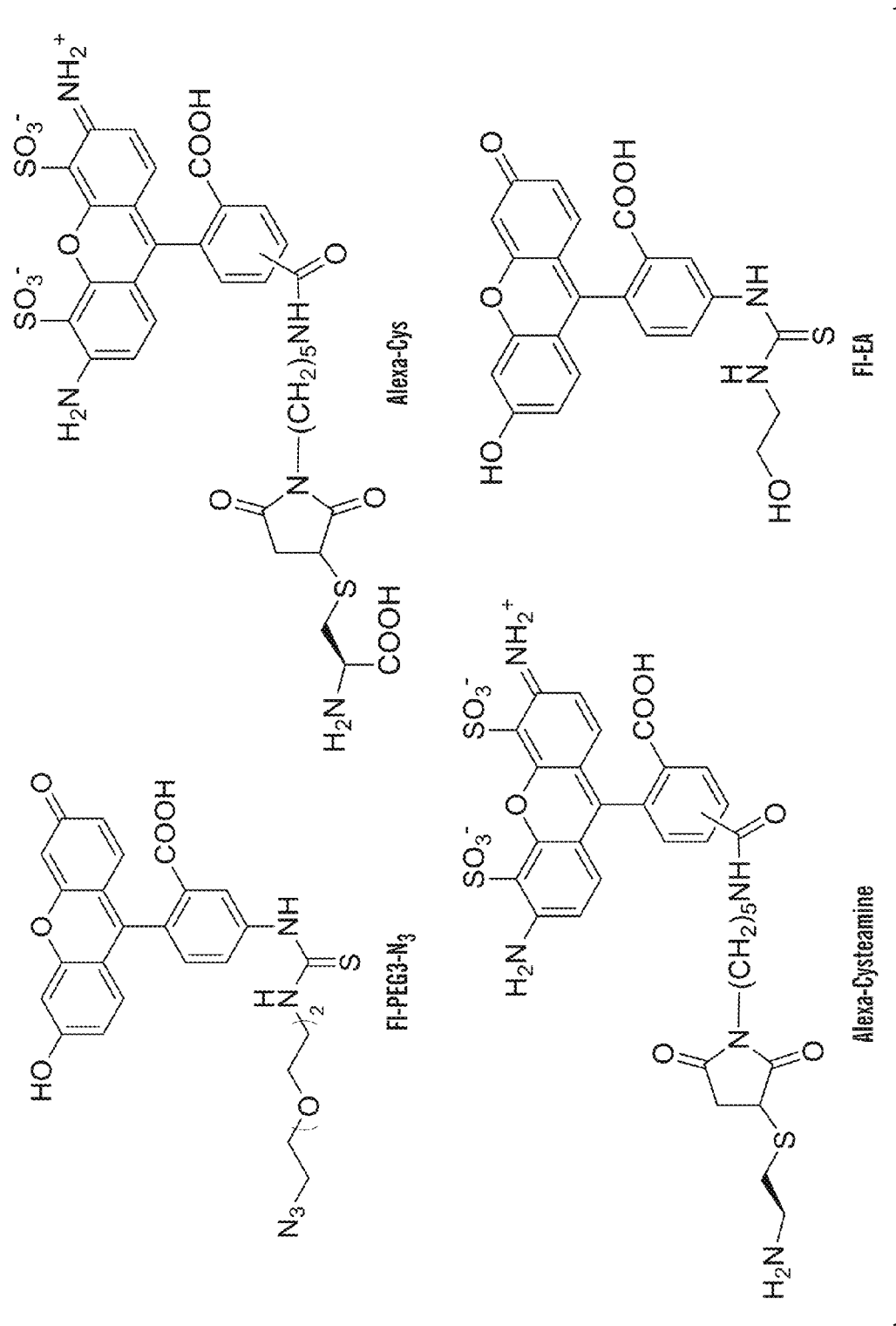
FIG. 7 is a series of graphs depicting flow-cytometry results of three dye derivatives staining Jurkat cells. The top row displays the structures of these molecules; the middle row shows results for CPT treated cells; the bottom row shows results for CPT untreated cells. Each column is correlated to the molecule present in the top row.
Figure 7:
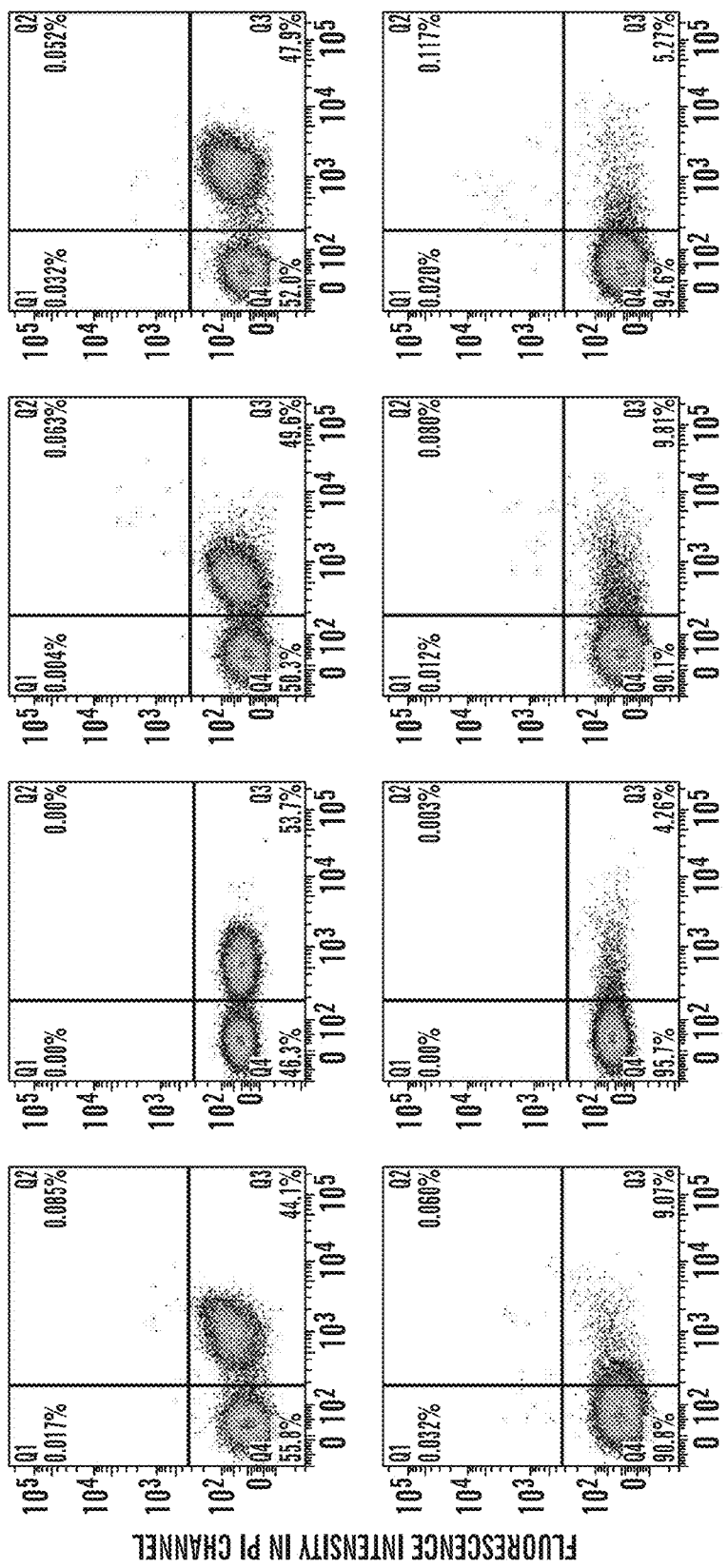
Figure 8A:
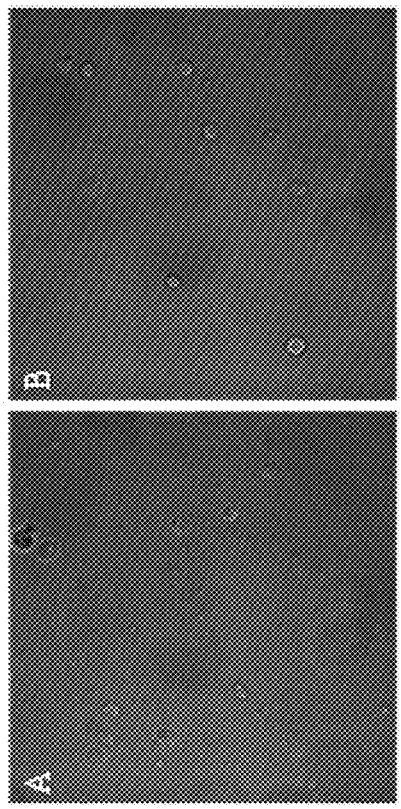
FIGS. 8A-8D are a series of micrographs depicting confocal microscopy images of Rhodamine B and Rd-EA staining Jurkat cell samples.
Figure 8B:
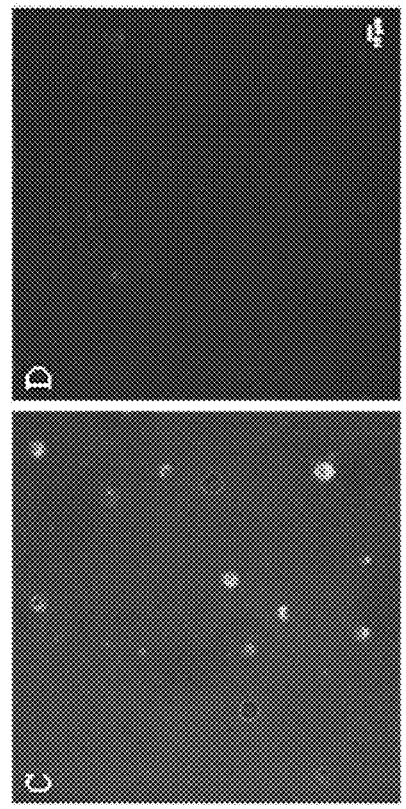
Figure 8C:
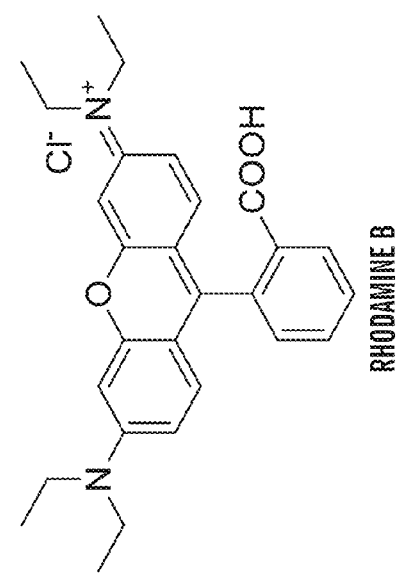
Figure 8D:
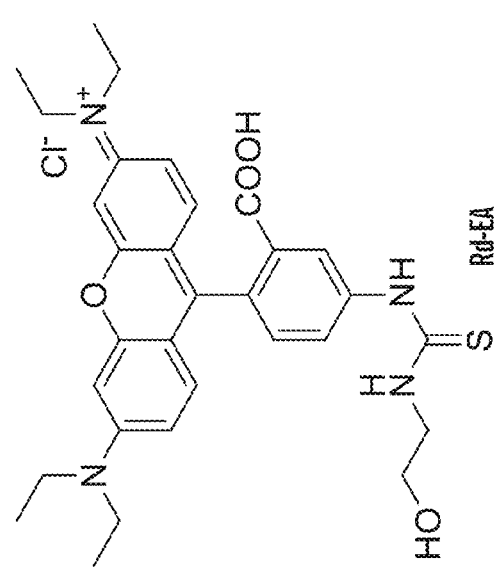

Further exploration revealed a number of derivatives of commonly used dyes that are capable of selective entry into apoptotic cells (FIG. 3A and FIG. 7). For example, FITC reacting with a long-chain amine yields the compound F1-PEG3-N$_3$, which readily stains the apoptotic cells as F1-EA does. Similarly, the two derivatives of Alexa Fluor® 488 (Alexa-Cys and Alexa-Cysteamine) successfully label the apoptotic population of Jurkat cells upon CPT treatment. These three compounds display a net charge of −1, -2, and -1 respectively. Moreover, the ethanolamine derivative of rhodamine B isothiocyanate (Rh-EA, net charge zero) preferentially stains the apoptotic cells as well (FIGS. 8A-8D). This group of apoptosis markers, although sharing the same carbon skeleton, displays various functional groups and a net charge ranging from −2 to 0. Their similar behavior of cell entry indicates that the functional group and net charge are not the determining factors of membrane permeability of apoptotic cells.

Figure 3B:
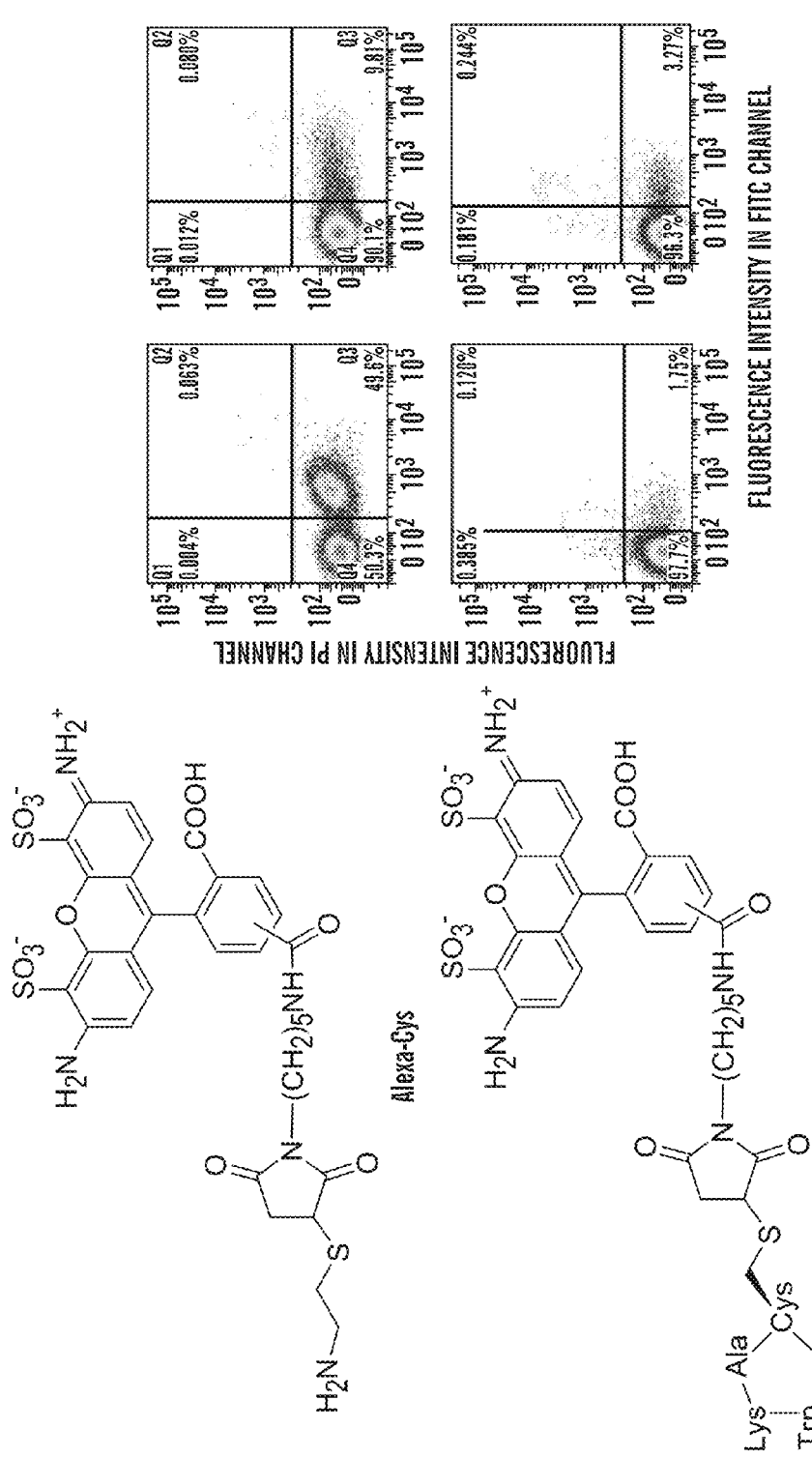

The inventors further explored the scope of apoptotic cell-permeable molecules by conjugating cyclic peptides of various sizes onto the fluorophores. Specifically, three conjugates of Alexa Fluor® 488 were prepared that carry cyclic peptides of five, eight, and eleven residues respectively (FIG. 3B). The cyclic peptides only differ in the number of alanine residues included in their sequence. These Alexa-peptide conjugates were designed to display the same net charge with Alexa-Cysteamine. However, in sharp contrast to Alexa-Cysteamine, even the conjugate with the smallest cyclic peptide was unable to enter apoptotic cells, indicating a rather narrow window of molecular size is allowed for apoptotic cell entry.

Figure 4:
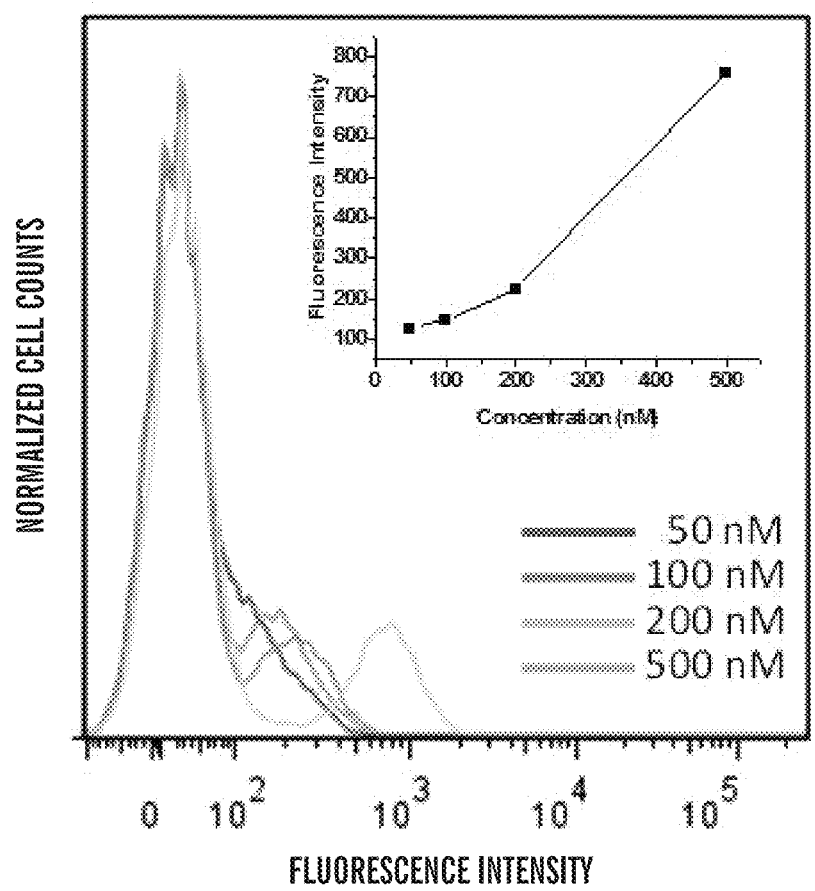
FIG. 4 is a graph depicting flow cytometry analysis of apoptotic cells stained with Alexa-Cys at varied concentrations. The mean fluorescence intensity of the apoptotic population increases with Alexa-Cys concentration (inset), indicating a passive diffusion mechanism of cell entry driven by the concentration gradient.
Figure 5A:
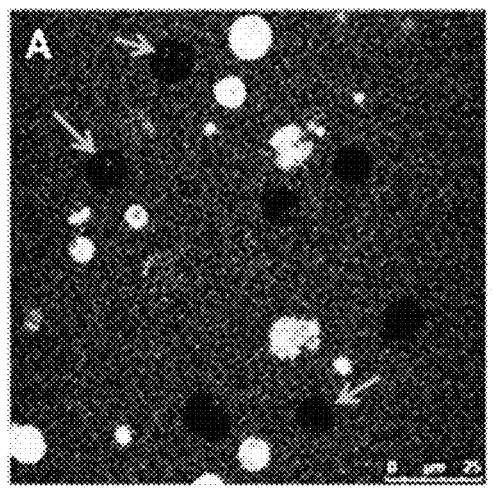
FIGS. 5A-5D are confocal microscopy images of F1-EA staining Jurkat cell samples without the washing step.
Figure 5B:
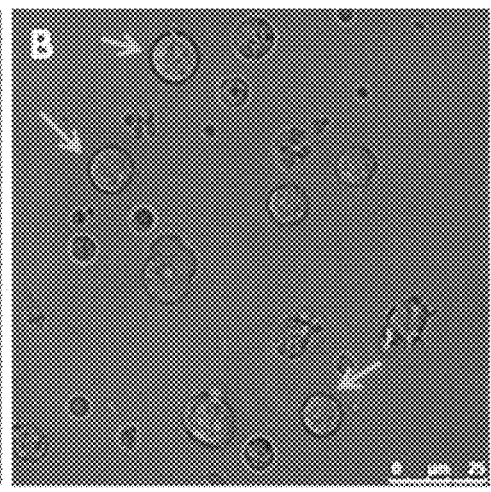
Figure 5C:
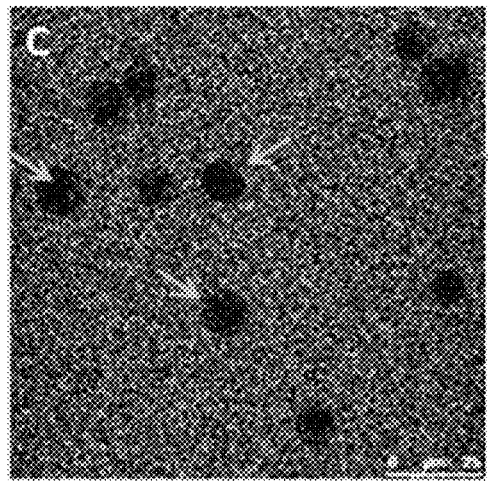
Figure 5D:
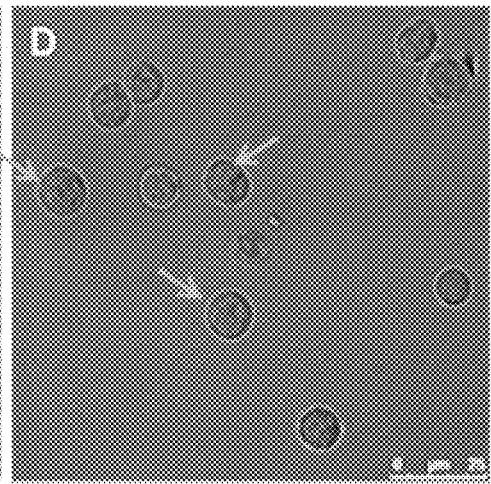
Figure 6A:
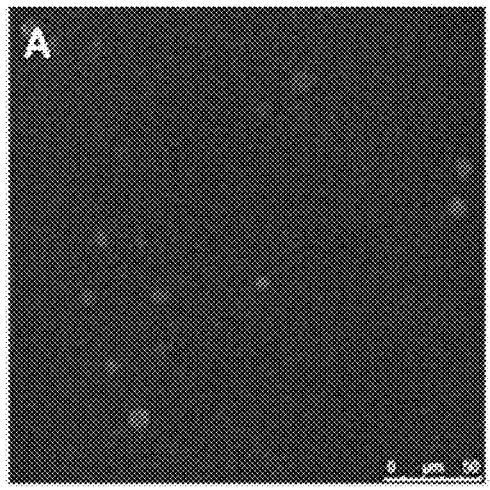
FIGS. 6A-6D are micrographs depicting representative confocal images.
Figure 6B:
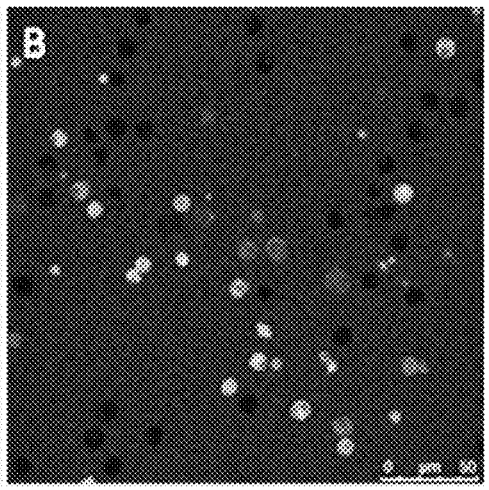
Figure 6C:
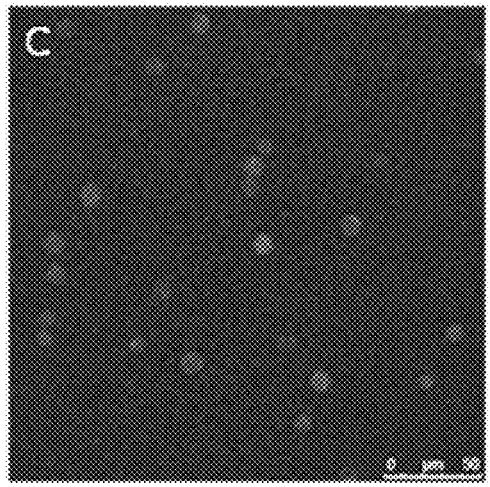
Figure 6D:
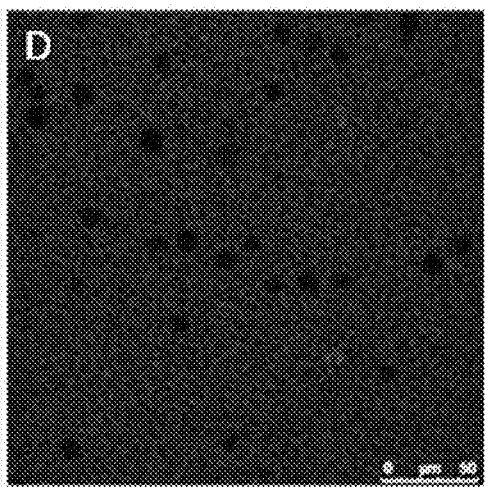
Figure 9:
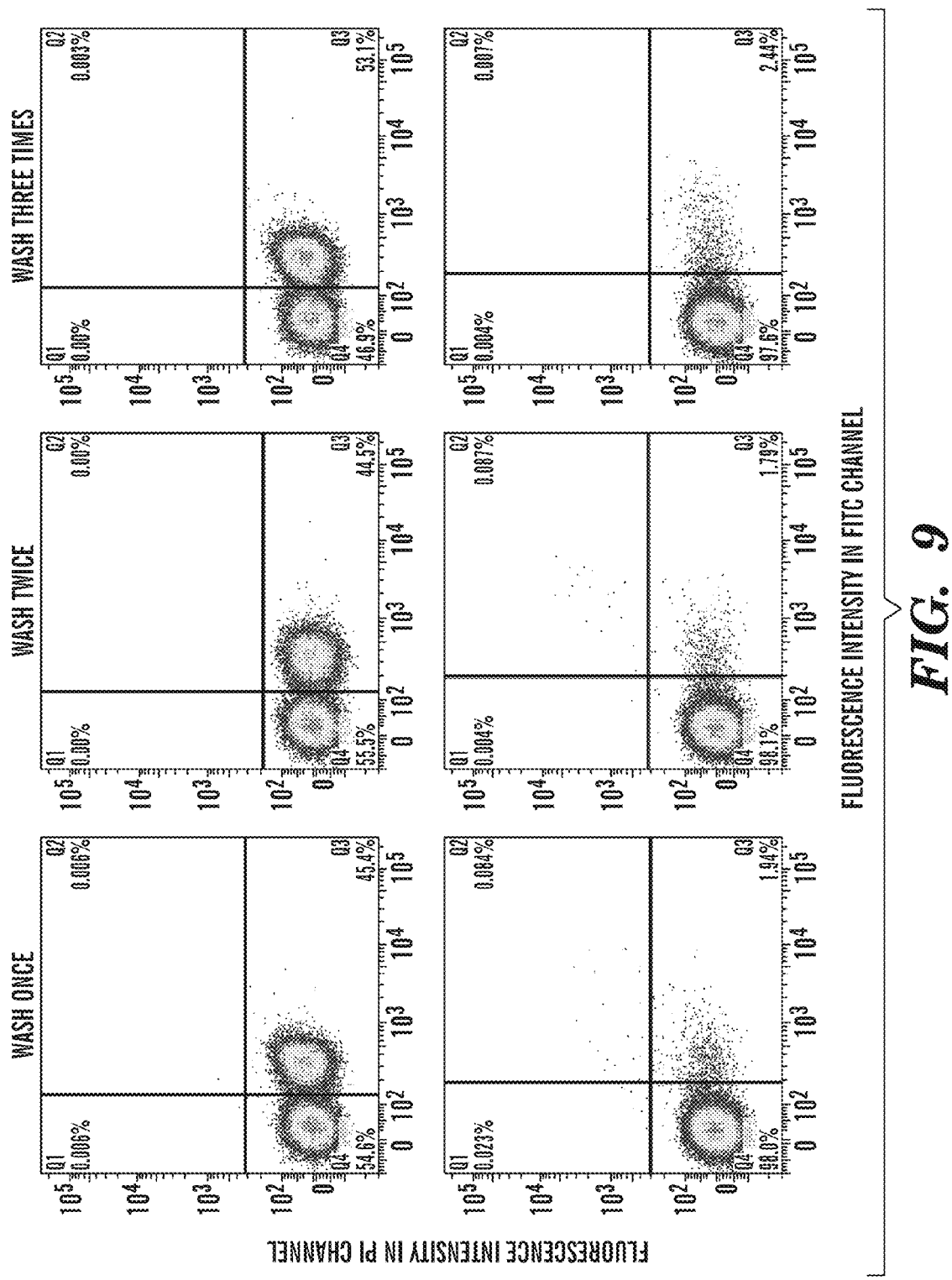
FIG. 9 is a series of graphs showing that increased washing times did not affect the fluorescence intensity of Alexa-Cys stained cell populations. Top row, CPT treated cells; bottom row, CPT untreated cells.

The mechanism of cell entry of these dye derivatives was also investigated by varying the concentration used to stain Jurkat cells. At 50, 100, 200, and 500 nM concentrations, Alexa-Cys identified essentially the same percentage of cells that were at early stages of apoptosis. Interestingly, increasing the concentration of Alexa-Cys correlated with an increased fluorescence intensity of the apoptotic population (FIG. 4), indicating that cell entry of Alexa-Cys is through passive diffusion driven by the concentration gradient. The membrane permeability of Alexa-Cys appeared to be irreversible: the fluorescence staining of apoptotic cells remained unchanged upon multiple washes with the fluorophore-free medium (FIG. 9). This observation indicates the fluorophore is incapable of escaping after its entry into apoptotic cells.

To date only a limited number of small molecules are known to selectively permeate into apoptotic cells. Among these are the commercially available Yo-Pro and To-Pro dyes, which detect cell death through membrane permeabilization and DNA intercalation (T. Idziorek et al., *J. Immunol. Methods*, 1995, 185, 249-258). More recently, several structurally unrelated molecules (dubbed ApoSense by the authors) were reported to effectively label apoptotic cells both in vitro and in vivo (M. Damianovich et al., *Eur J Nucl Med Mol Imaging*, 2006, 33, 281-291; R. Aloya et al., *Apoptosis*, 2006, 11, 2089-2101; A. Cohen et al., *Cell Res*, 2009, 19, 625-637). The physiochemical basis of their selectivity towards apoptotic cells remains largely unexplored save one recent report indicating the caspase-activated Pannexin channel may serve as a conduit for these small molecules entering apoptotic cells (F. B. Chekeni et al., *Nature*, 2010, 467, 863-867.).

The data provided herein represent the first systematic investigation on the structure-permeability relationship for apoptosis-specific molecules. The results show that the membrane of apoptotic cells grants entry to small molecules of varied structure and charge, but has a relatively stringent requirement on molecular size. Importantly, it is demonstrated for the first time that simple modification enables several members of the fluorescein family to gain selective entry into apoptotic cells, which significantly expands the arsenal of low-molecular weight reporters of apoptotic cell death. These results will greatly contribute to the design of further small molecule agents that enable noninvasive imaging of apoptosis in living organisms.

General Methods: Alexa Fluor® 488 C5 Maleimide was purchased from Invitrogen™ Fluorescein was purchased from Riedel-de Haën. Fluorescein 5(6)-isothiocyanate, Rhodamine β isothiocyanate and other common chemicals were purchased from Sigma-Aldrich™ (St. Louis, Mo.). PBS buffer, DMEM/High glucose media, RPMI 1640 media, and Pen/Strep were purchased from Thermal Scientific™ (Amarillo, Tex.). Fatty acid-free bovine serum albumin (BSA) and 0.25% Trypsin-EDTA solution were obtained from Invitrogen™ (Carlsbad, Calif.). Camptothecin (CPT) was from MP Biomedicals™ LLC (Solon, Ohio). PE-labeled and FITC-labeled annexin V (AV-PE and AV-FITC) and propidium iodide (PI) were purchased as an apoptotic cell detection kit from BD Biosciences™ (Chicago, Ill.). VALAP was prepared in house by melting and mixing equal amounts of Vaseline, Lanolin and paraffin wax, which were purchased from a local CVS Pharmacy™. MS data for the characterizations of the molecules were generated by Boston College Mass-Spec facilities. The concentration measurements were performed on a NanoDrop™ 2000c UV-Vis spectrometer from Thermo Scientific™ (Wilmington, Del.).

Expanding the Scope of Dye Derivatives that Selectively Target Apoptotic Cells

Cell staining results from four small molecules that behave similar to F1-EA are presented herein. The same protocol has been carried out for these molecules, including F1-PEG3-N$_3$, Alexa-Cys, Alexa-Cysteamine and Rd-EA to stain CPT treated and untreated Jurkat cells. The flow-cytometry results of F1-PEG3-N3, Alexa-Cys and Alexa-Cysteamine were identical to each other, as well as to that of F1-EA. (FIG. 7)

The confocal microscopy images confirmed that Rd-EA can selectively stain the apoptotic cell population. As negative control, Rhodamine B has no selectivity.

The Influence of Washing Times to Alexa-Cys Staining for Apoptotic Cells

Before preparing samples for the flow-cytometry, the Alexa-Cys stained cells were washed with PBS buffer for one, two and three times respectively. Each washing step included 20 mins incubation to ensure the small molecule to reach the equilibrium. (FIG. 9). Increased washing times did not affect the fluorescence intensity of Alexa-Cys cell populations.

The invention claimed is:

1. An assay for detecting apoptosis in a biological sample comprising a cell, the method comprising:
analyzing a biological sample comprising a cell for the presence of a fluorescent cell, wherein the biological sample was contacted with a fluorescent compound of formula (I)

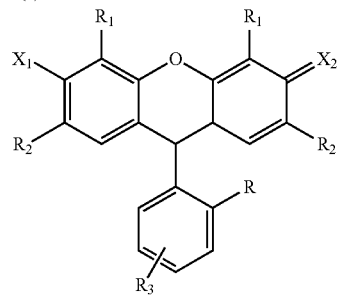

wherein
R$_1$ is hydrogen, SO$_3^-$, OH, OR$_5$; COOH, COOR$_5$, NH$_2$, or N(R$^B$)$_2$;
X$_1$ is OH, NH$_2$, N(R$_7$R$_8$); CF$_3$, CN, C(O)R$^B$, CO$_2$R$^B$, C(O)N(R$^B$)$_2$, OR$^B$, N(R$^B$)$_2$, N=C=S, NHC(O)R$^B$, NHC(O)OR$^B$, NHC(S)R$^B$, NHC(S)N(R$^B$)$_2$, NHSO$_2$R$^B$, NHSO$_2$N(R$^B$)$_2$, NO$_2$, N$_2$—R$^B$, SOR$^B$, SO$_2$R$^B$, SO$_3$R$^B$, OP(O)(OH)$_2$, optionally substituted linear or branched C$_1$-C$_{10}$ alkyl, optionally substituted linear or branched C$_2$-C$_{10}$ alkenyl, optionally substituted linear or branched C$_2$-C$_{10}$ alkynyl, optionally substituted cyclyl, optionally substituted heterocyclyl, optionally substituted aryl, and optionally substituted heteroaryl;
X$_2$ is O, NH$_2$, or N(R$_7$R$_8$);
each R$_2$ is independently hydrogen, halogen, CF$_3$, alkyl, OH, or taken together with either X$_1$ or X$_2$ forms optionally substituted carbocyclic, optionally substituted heterocyclic, optionally substituted aryl, or optionally substituted heteroaryl;
R$_3$ is C(O)R$_4$, or N(H)R$_4$;

R₄ is hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^B$; OH; $OR^B$; —NH($R^B$); —N($R^B$)₂; —C(=O)NH($R^B$); —C(=O)N($R^B$)₂; —C(=S)NH($R^B$); —C(=S)N($R^B$)₂;

each $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

R₅ is a protecting group; aliphatic; heteroaliphatic; acyl; aryl moiety; or heteroaryl; and each R₇ and R₈ is independently hydrogen, or alkyl;

R is hydrogen, $C_{1-6}$alkyl, or COOR₉;

R₉ is hydrogen, or $C_{1-4}$alkyl, wherein the compound formula (I) selectively labels apoptotic cells and does not level non-apoptotic cells, and wherein the presence of a fluorescent cells permits detection of apoptotic in the biological sample.

2. The assay of claim 1, wherein the compound of Formula (I) is selected from the group consisting of Formula Formula (IIa)

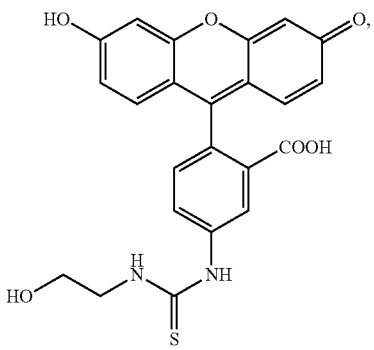

IIa

Formula (IIIa)

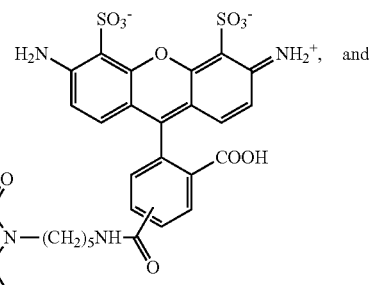

IIIa and

Formula (IIIb)

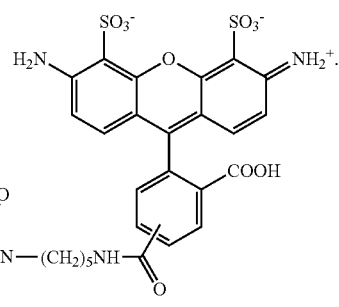

IIIb

3. The assay of claim 1, wherein the biological sample is obtained from a subject.

4. The assay of claim 3, wherein the biological sample remains in situ or in vivo.

5. The assay of claim 4, wherein the subject has a tumor or a cancer.

6. The assay of claim 5, wherein the subject is currently undergoing treatment with an anti-cancer agent.

7. The assay of claim 5, wherein the subject was previously treated with an anti-cancer agent.

8. The assay of claim 1, wherein the biological sample is contacted with the fluorescent compound in vitro.

* * * * *